US012171817B2

(12) United States Patent
Sibley et al.

(10) Patent No.: US 12,171,817 B2
(45) Date of Patent: Dec. 24, 2024

(54) ANTIGENS FOR DETECTING TOXOPLASMA INFECTION BY MONITORING CELLULAR IMMUNITY

(71) Applicant: Washington University, St. Louis, MO (US)

(72) Inventors: Laurence David Sibley, St. Louis, MO (US); Kevin M. Brown, St. Louis, MO (US); Qiuling Wang, St. Louis, MO (US); Iti Saraav, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 18/464,051

(22) Filed: Sep. 8, 2023

(65) Prior Publication Data

US 2024/0091327 A1    Mar. 21, 2024

Related U.S. Application Data

(62) Division of application No. 17/742,023, filed on May 11, 2022, now abandoned, which is a division of application No. 16/347,510, filed as application No. PCT/US2017/059978 on Nov. 3, 2017, now Pat. No. 11,351,233.

(60) Provisional application No. 62/417,136, filed on Nov. 3, 2016, provisional application No. 62/550,393, filed on Aug. 25, 2017.

(51) Int. Cl.
G01N 33/53      (2006.01)
A61K 39/00      (2006.01)
A61K 39/002     (2006.01)
A61M 5/315      (2006.01)

(52) U.S. Cl.
CPC ........ *A61K 39/0002* (2013.01); *A61K 39/002* (2013.01); *A61M 5/31531* (2013.01); *A61K 2039/54* (2013.01); *A61K 2039/572* (2013.01); *A61K 2039/6087* (2013.01)

(58) Field of Classification Search
None
See application file for complete search history.

(56) References Cited

U.S. PATENT DOCUMENTS

2010/0203085 A1    8/2010  Bzik

FOREIGN PATENT DOCUMENTS

| CN | 104897891 A | 9/2015 |
|----|-------------|--------|
| EP | 2889040 A1 | 7/2015 |
| WO | 0164243 A2 | 9/2001 |
| WO | 2018085685 A1 | 5/2018 |
| WO | 2021034963 A1 | 2/2021 |

OTHER PUBLICATIONS

Lourenco et al (Microbes and Infection. 2006. 8: 12441251).*
Beghetto et al (The J. Infect. Dis. 2005. 191: 637-645).*
Vukmanovic-Stejic M., et al., "Mantoux Test as a Model for a Secondary Immune Response in Humans," Immunology Letters, 2006, vol. 107, No. 2, pp. 93-101.
Wang P., et al., "A Systematic Assessment of MHC Class II Peptide Binding Predictions and Evaluation of a Consensus Approach," PLOS Computational Biology, 2008, vol. 4, No. 4, Article e1000048, pp. 1-10, Published: Apr. 4, 2008.
Allen I.C., "Delayed-type Hypersensitivity Models in Mice," Methods in Molecular Biology, Mouse Models of Innate Immunity: Methods and Protocols, Chapter 13, Springer Science+Business Media, LLC, 2013, vol. 1031, pp. 101-107, doi: 10.1007/978-1-62703-481-4_13, XP055534072.
Behnke M.S., et al., "Coordinated Progression Through Two Subtranscriptoms Underlies the Tachyzoite Cycle of Toxoplasma Gondii," Plos One, Published on Aug. 26, 2010, vol. 5, No. 8, e12354, 20 Pages.
Black C.A., "Delayed Type Hypersensitivity: Current Theories With a Historic Perspective," Dermatology Online Journal, 1999, vol. 5, No. 1:7, 11 Pages.
Blumenschein T.M.A., et al., "Atomic Resolution Insight Into Host Cell Recognition by Toxoplasma Gondii," The EMBO Journal, 2007, vol. 26, No. 11, pp. 2808-2820.
Brecht S., et al., "The Toxoplasma Micronemal Protein MIC4 is an Adhesin Composed of Six Conserved Apple Domains," The Journal of Biological Chemistry, Feb. 9, 2001, vol. 276, No. 6, pp. 4119-4127.
Brown K.M., et al., "Serum Albumin Stimulates Protein Kinase G-Dependent Microneme Secretion in Toxoplasma gondii," The Journal of Biological Chemistry, Apr. 29, 2016, vol. 291, No. 18, pp. 9554-9565.
Brydges S.D., et al., "Molecular Characterization of TgMIC5, a Proteolytically Processed Antigen Secreted from the Micronemes of Toxoplasma Gondii," Molecular and Biochemical Parasitology, Nov. 2000, vol. 111, No. 1, pp. 51-66.
Carruthers V.B., et al., "Secretion of Micronemal Proteins is Associated with Toxoplasma Invasion of Host Cells," Cellular Microbiology, 1999, vol. 1, No. 3, pp. 225-235.
Carruthers V.B., et al., "Sequential Protein Secretion From Three Distinct Organelles of Toxoplasma Gondii Accompanies Invasion of Human Fibroblasts," European Journal of Cell Biology, Jun. 1997, vol. 73, pp. 114-123.
Carruthers V.B., et al., "Ethanol and Acetaldehyde Elevate Intracellular [Ca2+] Calcium and Stimulate Microneme Discharge in Toxoplasma Gondii," Biochemical Journal, 1999, vol. 342, pp. 379-386.

(Continued)

Primary Examiner — Jennifer E Graser
(74) Attorney, Agent, or Firm — Polsinelli PC

(57) ABSTRACT

Antigens of *Toxoplasma gondii* that provide specific and strong delayed type hypersensitivity (DTH) immune response, or which stimulate IFN-γ secretion, are used for testing subjects for infection. Any skin testing format may be adapted for testing for the delayed type hypersensitivity, including a patch, a needle, or a prong. Presence of DTH indicates infection. Alternate methods of detecting a T cell response including monitoring IFN-γ secretion may be used.

7 Claims, 5 Drawing Sheets
(4 of 5 Drawing Sheet(s) Filed in Color)
Specification includes a Sequence Listing.

(56) References Cited

OTHER PUBLICATIONS

Carruthers V.B., et al., "Mobilization of Intracellular Calcium Stimulates Microneme Discharge in Toxoplasma Gondii," Molecular Microbiology, 1999, vol. 31, No. 2, pp. 421-428.
Cerede O., et al., "The Toxoplasma Gondii Protein MIC3 Requires Pro-Peptide Cleavage and Dimerization to Function as Adhesin," The EMBO Journal, 2002, vol. 21, No. 11, pp. 2526-2536.
Communication Pursuant to Article 94(3) EPC in European Application No. 17868052.6, mailed Jan. 27, 2021, 4 pages.
Communication Pursuant to Article 94(3) EPC in European Application No. 17868052.6, mailed Nov. 30, 2021, 4 pages.
Erskine C.L., et al., "MHC Class II Epitope Nesting Modulates Dendritic Cell Function and Improves Generation of Antigen-Specific CD4 Helper T Cells," Journal of Immunology, 2011, vol. 187, pp. 316-324.
Etheridge R.D., et al., "The Toxoplasma Pseudokinase ROP5 Forms Complexes with ROP18 and ROP17 Kinases that Synergize to Control Acute Virulence in Mice," Cell Host Microbe, May 14, 2014, vol. 15, pp. 537-550.
Extended European Search Report for European Application No. 17868052.6, mailed Mar. 30, 2020, 05 Pages.
Frenkel J.K., et al., "Dermal Hypersensitivity to Toxoplasma Antigens (Toxoplasmins)," Proceedings of the Society for Experimental Biology and Medicine, May-Jul.-Aug. 1948, vol. 68, pp. 634-639.
Friedrich N., et al., "Members of a Novel Protein Family Containing Microneme Adhesive Repeat Domains Act as Sialic Acid-binding Lectins during Host Cell Invasion by Apicomplexan Parasites," Journal of Biological Chemistry, Jan. 15, 2010, vol. 285, No. 3, pp. 2064-2076.
Garnett J.A., et al., "Detailed Insights From Microarray and Crystallographic Studies Into Carbohydrate Recognition by Microneme Protein 1 (MIC1) of Toxoplasma Gondii," Protein Science, 2009, vol. 18, No. 9, pp. 1935-1947.
Gross S., et al., "Bioluminescence Imaging of Myeloperoxidase Activity in Vivo," Nature Medicine, Apr. 2009, vol. 15, No. 4, pp. 455-461, 15 Pages, DOI:10.1038/nm.1886, XP055425864.
Hoff E.F., et al., "Toxoplasma Gondii: Molecular Cloning and Characterization of a Novel 18-kDa Secretory Antigen, TgMIC10," Experimental Parasitology, Feb. 2001, vol. 97, No. 2, pp. 77-88.
Hoffmann C., et al., "Evolving Characteristics of Toxoplasmosis in Patients Infected With Human Immunodeficiency Virus-1: Clinical Course and Toxoplasma Gondii-specific Immune Responses," Clinical Microbiology and Infectious Diseases, May 2007, vol. 13, No. 5, pp. 510-515.
Holec L., et al., "Toxoplasma Gondii: Enzyme-linked Immunosorbent Assay Using Different Fragments of Recombinant Microneme Protein 1 (MIC1) for Detection of Immunoglobulin G Antibodies," Journal of Experimental Parasitology, Science Direct, May 2008, vol. 119, No. 1, pp. 1-6.
Holec-Gasior L., et al., "MIC1-MAG1-SAG1 Chimeric Protein, a Most Effective Antigen for Detection of Human Toxoplasmosis," Clinical and Vaccine Immunology, Dec. 2012, vol. 19, No. 12, pp. 1977-1979.
Holec-Gasior L., "Toxoplasma Gondii Recombinant Antigens as Tools for Serodiagnosis of Human Toxoplasmosis: Current Status of Studies," Clinical and Vaccine Immunology, Sep. 2013, vol. 20, No. 9, pp. 1343-1351.
Huynh M-H., et al., "Rapid Invasion of Host Cells by Toxoplasma Requires Secretion of the MIC2-M2AP Adhesive Protein Complex," The EMBO Journal, 2003, vol. 22, No. 9, pp. 2082-2090.
International Preliminary Report on Patentability for International Application No. PCT/US2017/059978, mailed May 16, 2019, 9 pages.
International Search Report and Written Opinion for International Application No. PCT/US2017/059978, mailed Jan. 26, 2018, 11 Pages.
International Search Report and Written Opinion for International Application No. PCT/US2020/047048, mailed Jan. 15, 2021, 10 Pages.
Ismael A.B., et al., "The MIC3 Gene of Toxoplasma Gondii is a Novel Potent Vaccine Candidate Against Toxoplasmosis," Infection and Immunity, Nov. 2003, vol. 71, No. 11, pp. 6222-6228, DOI: 10.1128/IAI.71.11.6222-6228.2003, XP009173136.
Jacobs D.M., et al., "Inhibition of the Mitogenic Response to Lipopolysaccharide (LPS) in Mouse Spleen Cells by Polymyxin B," The Journal of Immunology, Jan. 1977, vol. 118, No. 1, pp. 21-27.
Khan A., et al., "Geographic Separation of Domestic and Wild Strains of Toxoplasma Gondii in French Guiana Correlates with a Monomorphic Version of Chromosome 1a," PLOS Neglected Tropical Diseases, Sep. 2014, vol. 8, No. 9, e3182, pp. 1-12.
Kong J-T., et al., "Serotyping of Toxoplasma Gondii Infections in Humans Using Synthetic Peptides," The Journal of Infectious Diseases, May 1, 2003, vol. 187, No. 9, pp. 1484-1495.
McCulloch W.F., et al., "Studies on Medical and Veterinary Students Skin Tested for Toxoplasmosis," Public Health Reports, Aug. 1963, vol. 78, No. 8, pp. 689-698.
Mercier C., et al., "Toxoplasma Secretory Granules: One Population or More?," Trends in Parasitology, 2015, vol. 31, No. 2, 12 Pages.
Moire N., et al., "Mic1-3KO Tachyzoite a Live Attenuated Vaccine Candidate Against Toxoplasmosis Derived From a Type I Strain Shows Features of Type II Strain," Experimental Parasitology, 2009, vol. 123, pp. 111-117.
Nielsen M., et al., "MHC Class II Epitope Predictive Algorithms," Immunology, 2010, vol. 130, pp. 319-328, Doi: 10.1111/j.1365-2567.2010.03268.x, XP055256448.
Office Action for European Patent Application No. 17868052.6, mailed on Jan. 30, 2023, 4 pages.
Petsch D., "Endotoxin Removal from Protein Solutions, "Journal of Biotechnology, 2000, vol. 76, No. 2-3, pp. 97-119, DOI:10.1016/S0168-1656(99)00185-6, XP002296265.
Philpott D.J., et al., "The Role of Toll-like Receptors and Nod Proteins in Bacterial Infection," Molecular Immunology, 2004, vol. 41, pp. 1099-1108, DOI:10.1016/j.molimm.2004.06.012, XP004596737.
Pinzan C.F., et al., "Vaccination with Recombinant Microneme Proteins Confers Protection against Experimental Toxoplasmosis in Mice," PLoS One, Nov. 17, 2015, vol. 10, No. 11, pp. 1-18.
Reiss M., et al., "Identification and Characterization of an Escorter for Two Secretory Adhesins in Toxoplasma Gondii," The Journal of Cell Biology, Feb. 5, 2001, vol. 152, No. 3, pp. 563-578, XP055794982.
Rougier D., et al., "Detection of Toxoplasmic Immunity by Multipuncture Skin Test with Excretory-Secretory Antigen," The Lancet, Jul. 20, 1985, vol. 2, No. 8447, pp. 121-123.
Saouros S., et al., "A Novel Galectin-like Domain from Toxoplasma Gondii Micronemal Protein 1 Assists the Folding, Assembly, and Transport of a Cell Adhesion Complex," Journal of Biological Chemistry, Nov. 18, 2005, vol. 280, No. 46, pp. 38583-38591.
Saraavi., et al., "Secretory Microneme Proteins Induce T-Cell Recall Responses in Mice Chronically Infected with Toxoplasma Gondii," mSphere, Jan./Feb. 2019, vol. 4, No. 1, e00711-e00718, 13 pages.
Sawmynaden K., et al., "Structural Insights Into Microneme Protein Assembly Reveal a New Mode of EGF Domain Recognition," EMBO Reports, 2008, vol. 9, No. 11, pp. 1149-1155.
Sedgwick J.D., et al., "A Solid-Phase Immunoenzymatic Technique for the Enumeration of Specific Antibody-Secreting Cells," Journal of Immunological Methods, 1983, vol. 57, No. 1-3, pp. 301-309, Doi: 10.1016/0022-1759(83) 90091-1, XP025224877.
Sioud M., et al., "A Novel Peptide Carrier for Efficient Targeting of Antigens and Nucleic Acids to Dendritic Cells," FASEB Journal, 2013, vol. 27, No. 8, pp. 3272-3283, Doi: 10.1096/fj.12-224758, XP055154760.
Veprekova A., "Approximative Molecular Weight of the Active Component in Toxoplasmin," Folia Parasitologica (Praha), 1978, vol. 25, pp. 273-275.

* cited by examiner

| Protein | Molecular Mass (kDa) | Endotoxin level (EU/mL) Before | Endotoxin level (EU/mL) After |
|---|---|---|---|
| MIC-1 | 48.6 | 2.878 | 0.051 |
| MIC 3 | 40.5 | 3.209 | 0.048 |
| MIC 4 | 63.0 | 3.212 | 0.068 |
| MIC 6 | 36.7 | 3.003 | 0.053 |
| SUMO | 12.5 | 3.124 | 0.071 |

```
                              SEQUENCE LISTING

Sequence total quantity: 64
SEQ ID NO: 1            moltype = AA  length = 456
FEATURE                 Location/Qualifiers
source                  1..456
                        mol_type = protein
                        organism = Toxoplasma gondii
SEQUENCE: 1
MGQALFLTVL LPVLFGVGPE AYGEASHSHS PASGRYIQQM LDQRCQEIAA ELCQGGLRKM   60
CVPSSRIVAR NAVGITHQNT LEWRCFDTAS LLESNQENNG VNCVDDCGHT IPCPGGVHRQ  120
NSNHATRHEI LSKLVEEGVQ RFCSPYQASA NKYCNDKFPG TIARRSKGFG NNVEVAWRCY  180
EKASLLYSVY AECASNCGTT WYCPGGRRGT STELDKRHYT EEEGIRQAIG SVDSPCSEVE  240
VCLPKDENPP VCLDESGQIS RTGGGPPSQP PEMQQPADRS DERGGGKEQS PGGEAQPDHP  300
TKGGNIDLPE KSTSPEKTPK TEIHGDSTKA TLEEGQQLTL TFISTKLDVA VGSCHSLVAN  360
FLDGFLKFQT GSNSAFDVVE VEEPAGPAVL TIGLGHKGRL AVVLDYTRLN AALGSAAYVV  420
EDSGCSSSEE VSFQGVGSGA TLVVTTLGES PTAVSA                           456

SEQ ID NO: 2            moltype = AA  length = 321
FEATURE                 Location/Qualifiers
source                  1..321
                        mol_type = protein
                        organism = Toxoplasma gondii
SEQUENCE: 2
MAYGEASHSH SPASGRYIQQ MLDQRCQEIA AELCQGGLRK MCVPSSRIVA RNAVGITHQN   60
TLEWRCFDTA SLLESNQENN GVNCVDDCGH TIPCPGGVHR QNSNHATRHE ILSKLVEEGV  120
QRFCSPYQAS ANKYCNDKFP GTIARRSKGF GNNVEVAWRC YEKASLLYSV YAECASNCGT  180
TWYCPGGRRG TSTELDKRHY TEEEGIRQAI GSVDSPCSEV EVCLPKDENP PVCLDESGQI  240
SRTGGGPPSQ PPEMQQPADR SDERGGGKEQ SPGGEAQPDH PTKGGNIDLP EKSTSPEKTP  300
KTEIHGDSTK ATLEEGQQLT L                                           321

SEQ ID NO: 3            moltype = DNA  length = 1920
FEATURE                 Location/Qualifiers
source                  1..1920
                        mol_type = other DNA
                        organism = Toxoplasma gondii
SEQUENCE: 3
acctgaaagc gggtgccgcg tcgctaccgt ttcctgtggc gtctctagtg cgacatccga    60
agtaacagta acgtccggca tggaacgccg acgcgggtgt tccagtcgcc tggctccttc   120
tactcgcact tcgatgttac gttccttatt ggtgcgacgc ggttctcgtg ttgctagacg   180
tcgcaccggc tgaaagctgt agaaaattta gttatttttcc tgtcagctag cttgcaggag   240
tgcgtttttg tgtgttggtt tcgtctcaca tggctgctga tctgttgatg cagctgtgta   300
cacgtgcctc gattctgtag ttgacctaga acggatttgc aaagatgggc caggcgttgt   360
ttctcaccgt tctattgccg gtgttatttg gcgttgggcc agaagcatat ggagaagcgt   420
cgcattctca ttcgccggca tcgggacgtt atatacaaca gatgcttgac caacgctgcc   480
aagagattgc tgcagaactc tgccaaggcg gacttcgtaa aatgtgtgtg ccctctagcc   540
ggatagtagc tcgaaacgcc gtgggcatta ctcatcaaaa tacacttgaa tggagatgcc   600
ttgatacagc ctctttgctg gagagcaatc aagaaaacaa cggtgttaat tgcgtggacg   660
actgtggcca cacgataccg tgtcctggcg gcgtacaccg gcaaaacagt aatcacgcaa   720
cgcgccatga gatactgtcc aaattggtcg aagaaggagt acaacggttc tgcagtcctt   780
atcaagcatc tgccaacaag tactgtaacg acaaatttgc agggaccatt gcgaggaggt   840
cgaagggctt cggaaacaat gtcgaggttg cgtggaggtg ttacgagaag gccagcttgc   900
tgtactcggt ttatgctgag tgtgcgagca actgcgaac aacgtggtac tgccctggag   960
gacgacgagg gacgtcgaca gaactagaca agcggcatta tacagaagag gaggaattc   1020
gccaggcaat cggatccgtc gacagcccat gttctgaagt tgaagtctgc ctaccgaagg  1080
atgagaatcc cccggtgtgt ttagatgaaa gtggccagat ttcgaact ggttggtgggc  1140
caccgtcaca accgcctgag atgcaacagc ccgccgatcg ttcggacgag agaggtggcg  1200
gtaaggaaca gtcgcctgga ggagaagctc agccggacca tccaacgaag ggtggtaaca  1260
tagacctgcc tgagaaatca acatctccg agaagacgcg aaaacgag atccatggtg   1320
acagcacgaa agcgacgtc gaagagggc actcacgttt atctccacta                1380
aactggatgt tgctgtaggc tcgtgtcatt cactcgtcgc gaatttcctt gatgatttt   1440
tgaagttttca gacgggctca aattcggcgt tcgatgtggt agaagtggaa gagccagcag  1500
gacccgcagt gcttacgata ggtctgggac acaaaggccg tctcgctgtt gtcctcgact  1560
acaccaggct caatgctgct ttaggatcag ctgcttacgt ggtcgaagat tctggatgca  1620
```

-continued

```
gctcaagtga agaggttagt ttccaaggag tgggtagtgg agcgacgctc gtggtgacga    1680
cgcttggcga gagtcctacg gccgtctctg cttgatttat agtactcttt ggagcatgct    1740
tgtggaggaa cgggacaatc tcggcaaaat caggatgaag tttgtgagat acagatcgtt    1800
cctgaacagt ggaagatgcg tcactattac acctatatgc gtcctggttc ttgtagagtt    1860
ggagttcttg caggtgtaat gactatgaca tacggatata acttcatacg gggaactgtg    1920

SEQ ID NO: 4              moltype = DNA   length = 48
FEATURE                   Location/Qualifiers
source                    1..48
                          mol_type = unassigned DNA
                          organism = Toxoplasma gondii
SEQUENCE: 4
actgtggtct ctaggtatgg aagcatatgg agaagcgtcg cattctca                   48

SEQ ID NO: 5              moltype = DNA   length = 49
FEATURE                   Location/Qualifiers
source                    1..49
                          mol_type = unassigned DNA
                          organism = Toxoplasma gondii
SEQUENCE: 5
actgttctag atcagagcgt tagttgctgc ccctcttcga gcgtcgctt                  49

SEQ ID NO: 6              moltype = AA    length = 198
FEATURE                   Location/Qualifiers
source                    1..198
                          mol_type = protein
                          organism = Toxoplasma gondii
SEQUENCE: 6
MALSSLNNIR PFSGLLGCGL LFGALVVVVA CVFSVPVEAG VLRKVAGAGS LQASIGEHDF      60
FNDYDQDEEY RKRQQELQNQ SPEEVEEAKR KYHEELRRKA EEDAETKRKQ EAVIQELKEV     120
AKKRGLREAA EREEKRIDEQ QANYEQRQQE LRDMDSAMEE RLMQQRKKDQ EERELARKNS     180
DKVMEELKEK LARRRKSM                                                  198

SEQ ID NO: 7              moltype = AA    length = 198
FEATURE                   Location/Qualifiers
source                    1..198
                          mol_type = protein
                          organism = Toxoplasma gondii
SEQUENCE: 7
MALSSLNNIR PFSGLLGCGL LFGALVVVVA CVFSVPVEAG VLRKVAGAGS LQASIGEHDF      60
FNDYDQDEEY RKRQQELQNQ SPEEVEEAKR KYHEELRRKA EEDAETKRKQ EAVIQELKEV     120
AKKRGLREAA EREEKRIDEQ QANYEQRQQE LRDMDSAMEE RLMQQRKKDQ EERELARKNS     180
DKVMEELKEK LARRRKSM                                                  198

SEQ ID NO: 8              moltype = DNA   length = 960
FEATURE                   Location/Qualifiers
source                    1..960
                          mol_type = unassigned DNA
                          organism = Toxoplasma gondii
SEQUENCE: 8
ttgtcggata gaacacatca aaaattttt ctgtttcatc tgtcacgtgc gtccttttgg       60
tggaagcgac gcgtcgtcgc ggccctgttg gggtagtca atatttcagt aagcgtttct     120
agcgacaccc gctacacaga acactcggtt gaagcactgt gatgctggcg tttctgtccg    180
ctgtctttct gcagaatggc gctttcttct ttgaacaata tcaggccttt tagcgggttg    240
ctgggttgcg gcctgctgtt tggcgccctt gtggtcgtgt tggcatgtgt tttcagcgtt    300
cctgtggaag caggcgttct tcgtaaggta gcaggtgcag gaagtctcca ggcgtctatt    360
ggagagcacg attttttaa cgattacgat caggacgagg aatacaggaa gcgccagcaa     420
gaactgcaga atcagagtcc agaagaagtc gaggaagcga aacgcaaata ccacgaagag     480
ctgagacgga aagcagaaga agatgcagag acgaaacgta agcaagaagc agtcattcaa     540
gaactgaaag aggtggcaaa gaaaagagga cttcgtgaag ccgctgagcg tgaggagaag    600
cgcattgatg agcagcaggc taattacgag caacgacaac aagaactgag agacatggat    660
tcagcaatgg aggagaggct tatgcagcag agaaaaaaag accaggaaga gagagaactt    720
gcaagaaaaa acagcgataa ggtcatggag gagctcaaag agaaactcgc aagacgcagg    780
aaatcaatgt agaagaaagg caagttctga ctagtgtatt aagtgtagca gcgtccgtt    840
attaccgtgt atacagggag atcgtcgttc agtttgaagt gtttattccg tgttgaaaga    900
agcgtttgtg taatgcagat gatcctgaga tgatagtgcg ggaaatcgaa tgactcattg    960

SEQ ID NO: 9              moltype = DNA   length = 41
FEATURE                   Location/Qualifiers
source                    1..41
                          mol_type = unassigned DNA
                          organism = Toxoplasma gondii
SEQUENCE: 9
actgtggtct ctaggtatgg cgctttcttc tttgaacaat a                          41

SEQ ID NO: 10             moltype = DNA   length = 38
FEATURE                   Location/Qualifiers
source                    1..38
                          mol_type = unassigned DNA
```

```
                        organism = Toxoplasma gondii
SEQUENCE: 10
actgttctag atcacattga tttcctgcgt cttgcgag                               38

SEQ ID NO: 11            moltype = AA   length = 236
FEATURE                  Location/Qualifiers
source                   1..236
                         mol_type = protein
                         organism = Toxoplasma gondii
SEQUENCE: 11
MARHAIFFAL CVLGLVAAAL PQFATAATAS DDELMSRIRN SDFFDGQAPV DSLRPTNAGV        60
DSKGTDDHLT TSMDKASVES QLPRREPLET EPDEQEEVHF RKRGVRSDAE VTDDNIYEEH       120
TDRKVVPRKS EGKRSFKDLL KKLALPAVGM GASYFAADRI LPELTEQQQT GEEPLTTGQN       180
VSTVLGFAAL AAAAAFLGMG LTRTYRHFSP RKNRSRQPAL EQEVPESGKD GEDARQ          236

SEQ ID NO: 12            moltype = AA   length = 236
FEATURE                  Location/Qualifiers
source                   1..236
                         mol_type = protein
                         organism = Toxoplasma gondii
SEQUENCE: 12
MARHAIFFAL CVLGLVAAAL PQFATAATAS DDELMSRIRN SDFFDGQAPV DSLRPTNAGV        60
DSKGTDDHLT TSMDKASVES QLPRREPLET EPDEQEEVHF RKRGVRSDAE VTDDNIYEEH       120
TDRKVVPRKS EGKRSFKDLL KKLALPAVGM GASYFAADRI LPELTEQQQT GEEPLTTGQN       180
VSTVLGFAAL AAAAAFLGMG LTRTYRHFSP RKNRSRQPAL EQEVPESGKD GEDARQ          236

SEQ ID NO: 13            moltype = DNA   length = 1120
FEATURE                  Location/Qualifiers
source                   1..1120
                         mol_type = unassigned DNA
                         organism = Toxoplasma gondii
SEQUENCE: 13
ttactttctt cggattacat tcttccacta aaagctggtt ttgtccagta tccattcgtc        60
gctaccgttg cgcagtcacg ttgaattttg cagcggcaaa acatcttgtg taaaattcga      120
gttttgttga tgattgaagt accctgtatt ggggcttgct aacgttttgt attaaaaggg      180
tttactgcgg cgtctcattt ccaaaatggc ccgacacgca attttttttcg cgctttgtgt    240
tttaggcctg gtggcggcgg ctttgccccca gttcgctacc gcggccaccg cgtcagatga     300
cgaactgatg agtcgaatcc gaaattctga ctttttcgat ggtcaagcac ccgttgacag      360
tctcagaccg acgaacgccg gtgtcagact caaagggaccg acgatccatc tcaccaccag     420
catggataag gcatctgtag agagtcagct tccgagaaga gagccattgg agacggagcc      480
agatgaacaa gaagaagttc atttcaggaa gcgaggcgtc cgttccgacg ctgaagtgac      540
tgacgacaac atctacgagg agcacactga tcgtaaagtg gttccgagga agtcggaggg      600
caagcgaagc ttcaaagact tgctgaagaa gctcgcgctg ccggctgttg gtatgggtgc      660
atcgtatttt gccgctgata gaattctgcc ggaactaaca gagcagcaac agacaggcga      720
agaaccccta accaccggcc agaatgtgag cactgtgtta ggcttcgcag cgcttgctgc      780
tgccgcagcg ttccttggca tgggtctcac gaggacgtac cgacatttttt ccccacgcaa     840
aaacagatca cggcagcctg cactcagagca agaggtgcct gaatcaggca aagatgggga      900
ggatgccccgc cagtaggata tgggggctaa taaaagtgag taggagctcg aggacagtgt     960
cccgaacgcg cctgagaggc agacagacac agaagagtga agaaaacaa catggtatta      1020
cgtgcggtga gtgtttgctg tcacgtgttt tttgcgccac aaagacagct tgtgttgtat     1080
gcatgggatc gacagttcat ggacggcgct acccagagag                            1120

SEQ ID NO: 14            moltype = DNA   length = 37
FEATURE                  Location/Qualifiers
source                   1..37
                         mol_type = unassigned DNA
                         organism = Toxoplasma gondii
SEQUENCE: 14
actgtgagga ctcaggtatg gctttgcccc agttcgc                                37

SEQ ID NO: 15            moltype = DNA   length = 35
FEATURE                  Location/Qualifiers
source                   1..35
                         mol_type = unassigned DNA
                         organism = Toxoplasma gondii
SEQUENCE: 15
actgttctag atcactggcg ggcatcctcc ccatc                                  35

SEQ ID NO: 16            moltype = DNA   length = 324
FEATURE                  Location/Qualifiers
source                   1..324
                         mol_type = unassigned DNA
                         organism = Toxoplasma gondii
SEQUENCE: 16
atgggtcatc accatcatca tcacgggtcc ctgcaggact cagaagtcaa tcaagaagct        60
aagccagagg tcaagccaga agtcaagcct gagactcaca tcaatttaaa ggtgtccgat      120
ggatcttcag atcttcttc aagatcaaa aagaccactc ctttaagaag gctgatggaa        180
gcgttcgcta aaagacaggg taaggaaatg gactccttaa gattcttgta cgacggtatt     240
agaattcaag ctgatcaggc ccctgaagat ttggacatgt aggataacga tattattgag     300
```

```
gctcaccgcg aacagattgg aggt                                                          324

SEQ ID NO: 17           moltype = AA  length = 108
FEATURE                 Location/Qualifiers
source                  1..108
                        mol_type = protein
                        organism = Toxoplasma gondii
SEQUENCE: 17
MGHHHHHHGS LQDSEVNQEA KPEVKPEVKP ETHINLKVSD GSSEIFFKIK KTTPLRRLME    60
AFAKRQGKEM DSLRFLYDGI RIQADQAPED LDMEDNDIIE AHREQIGG                108

SEQ ID NO: 18           moltype = AA  length = 456
FEATURE                 Location/Qualifiers
source                  1..456
                        mol_type = protein
                        organism = Toxoplasma gondii
SEQUENCE: 18
MGQALFLTVL LPVLFGVGPE AYGEASHSHS PASGRYIQQM LDQRCQEIAA ELCQGGLRKM    60
CVPSSRIVAR NAVGITHQNT LEWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGKEQS PGGEAQPDHP    300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 19           moltype = AA  length = 456
FEATURE                 Location/Qualifiers
source                  1..456
                        mol_type = protein
                        organism = Toxoplasma gondii
SEQUENCE: 19
MGQALFLTVL LPVLFGVGPE AYGEASHSHS PASGRYIQQM LDQRCQEIAA ELCQGGLRKM    60
CVPSSRIVAR NAVGITHQNT LEWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 20           moltype = AA  length = 456
FEATURE                 Location/Qualifiers
source                  1..456
                        mol_type = protein
                        organism = Toxoplasma gondii
SEQUENCE: 20
MGQALFLTVL LPVLFGVGPE AYGEASHSHS PASGRYIQQM LDQRCQEIAA ELCQGGLRKM    60
CVPSSRIVAR NAVGITHQNT LEWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 21           moltype = AA  length = 456
FEATURE                 Location/Qualifiers
source                  1..456
                        mol_type = protein
                        organism = Toxoplasma gondii
SEQUENCE: 21
MGQALFLTVL LPVLFGVGPE AYGEASHSHS PASGRYIQQM LDQRCQEIAA ELCQGGLRKM    60
CVPSSRIVAR NAVGITHQNT LEWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 22           moltype = AA  length = 456
FEATURE                 Location/Qualifiers
source                  1..456
                        mol_type = protein
                        organism = Toxoplasma gondii
SEQUENCE: 22
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
```

```
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 23           moltype = AA  length = 456
FEATURE                 Location/Qualifiers
source                  1..456
                        mol_type = protein
                        organism = Toxoplasma gondii
SEQUENCE: 23
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 24           moltype = AA  length = 456
FEATURE                 Location/Qualifiers
source                  1..456
                        mol_type = protein
                        organism = Toxoplasma gondii
SEQUENCE: 24
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 25           moltype = AA  length = 456
FEATURE                 Location/Qualifiers
source                  1..456
                        mol_type = protein
                        organism = Toxoplasma gondii
SEQUENCE: 25
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 26           moltype = AA  length = 456
FEATURE                 Location/Qualifiers
source                  1..456
                        mol_type = protein
                        organism = Toxoplasma gondii
SEQUENCE: 26
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 27           moltype = AA  length = 456
FEATURE                 Location/Qualifiers
source                  1..456
                        mol_type = protein
                        organism = Toxoplasma gondii
SEQUENCE: 27
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHQI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
```

```
FLDGFLKFQT GSNSAFDVVE VEEPAGPAVL TIGLGHKGRL AVVLDYTRLN AALGSAAYVV    420
EDSGCSSSEE VSFQGVGSGA TLVVTTLGES PTAVSA                              456

SEQ ID NO: 28            moltype = AA  length = 456
FEATURE                  Location/Qualifiers
source                   1..456
                         mol_type = protein
                         organism = Toxoplasma gondii
SEQUENCE: 28
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEDPAGPAVL TIGLGHKGRL AVVLDYTRLN AALGSAAYVV   420
EDSGCSSSEE VSFQGVGSGA TLVVTTLGES PTAVSA                             456

SEQ ID NO: 29            moltype = AA  length = 456
FEATURE                  Location/Qualifiers
source                   1..456
                         mol_type = protein
                         organism = Toxoplasma gondii
SEQUENCE: 29
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 30            moltype = AA  length = 456
FEATURE                  Location/Qualifiers
source                   1..456
                         mol_type = protein
                         organism = Toxoplasma gondii
SEQUENCE: 30
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 31            moltype = AA  length = 456
FEATURE                  Location/Qualifiers
source                   1..456
                         mol_type = protein
                         organism = Toxoplasma gondii
SEQUENCE: 31
MGQALFLTVL LPVLFGVGPE AYGEASHSHS PASGRYIQQM LDQRCQEIAA ELCQGGLRKM    60
CVPSSRIVAR NAVGITHQNT LEWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP VCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 32            moltype = AA  length = 456
FEATURE                  Location/Qualifiers
source                   1..456
                         mol_type = protein
                         organism = Toxoplasma gondii
SEQUENCE: 32
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 33            moltype = AA  length = 456
```

```
FEATURE                 Location/Qualifiers
source                  1..456
                        mol_type = protein
                        organism = Toxoplasma gondii
SEQUENCE: 33
MGQALFLTVL LPVLFGVGPE AYGEASHSHS PASGRYIQQM LDQRCQEIAA ELCQSGLRKM    60
CVPSSRIVAR NAVGITHQNT LQWRCFDTAS LLESNQENNG VNCVDDCGHT IPCPGGVHRQ   120
NSNHATRHEI LSKLVEEGVQ RFCSPYQASA NKYCNDKFPG TIARRSKGFG NNVEVAWRCY   180
EKASLLYSVY AECASNCGTT WYCPGGRRGT STELDKRHYT EEEGIRQAIG SVDSPCSEVE   240
VCLPKDENPP LCLDESGQIS RTGGGPPSQP PEMQQPADRS DERGGGKEQS PGGEAQPDHP   300
TKGGNIDLPE KSTSPEKTPK TEIHGDSTKA TLEEGQQLTL TFISTKLDVA VGSCHSLVAN   360
FLDGFLKFQT GSNSAFDVVE VEEPAGPAVL TIGLGHKGRL AVVLDYTRLN AALGSAAYVV   420
EDSGCSSSEE VSFQGVGSGA TLVVTTLGES PTAVSA                             456

SEQ ID NO: 34           moltype = AA  length = 198
FEATURE                 Location/Qualifiers
source                  1..198
                        mol_type = protein
                        organism = Toxoplasma gondii
SEQUENCE: 34
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 35           moltype = AA  length = 198
FEATURE                 Location/Qualifiers
source                  1..198
                        mol_type = protein
                        organism = Toxoplasma gondii
SEQUENCE: 35
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 36           moltype = AA  length = 198
FEATURE                 Location/Qualifiers
source                  1..198
                        mol_type = protein
                        organism = Toxoplasma gondii
SEQUENCE: 36
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 37           moltype = AA  length = 198
FEATURE                 Location/Qualifiers
source                  1..198
                        mol_type = protein
                        organism = Toxoplasma gondii
SEQUENCE: 37
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 38           moltype = AA  length = 198
FEATURE                 Location/Qualifiers
source                  1..198
                        mol_type = protein
                        organism = Toxoplasma gondii
SEQUENCE: 38
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 39           moltype = AA  length = 198
FEATURE                 Location/Qualifiers
source                  1..198
                        mol_type = protein
                        organism = Toxoplasma gondii
SEQUENCE: 39
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198
```

```
SEQ ID NO: 40            moltype = AA   length = 198
FEATURE                  Location/Qualifiers
source                   1..198
                         mol_type = protein
                         organism = Toxoplasma gondii
SEQUENCE: 40
MALSSLNNIR PFSGLLGCGL LFGALVVVVA CVFSVPVEAG VLRKVAGAGS LQASIGEHDF  60
FNDYDQDEEY RKRQQELQNQ SPEEVEEAKR KYHEELRRKA EEDAETKRKQ EAVIQELKEV 120
AKKRGLREAA EREEKRIDEQ QANYEQRQQE LRDMDSAMEE RLMQQRKKDQ EERELARKNS 180
DKVMEELKEK LARRRKSM                                              198

SEQ ID NO: 41            moltype = AA   length = 198
FEATURE                  Location/Qualifiers
source                   1..198
                         mol_type = protein
                         organism = Toxoplasma gondii
SEQUENCE: 41
MALSSLNNIR PFSGLLGCGL LFGALVVVVA CVFSVPVEAG VLRKVAGAGS LQASIGEHDF  60
FNDYDQDEEY RKRQQELQNQ SPEEVEEAKR KYHEELRRKA EEDAETKRKQ EAVIQELKEV 120
AKKRGLREAA EREEKRIDEQ QANYEQRQQE LRDMDSAMEE RLMQQRKKDQ EERELARKNS 180
DKVMEELKEK LARRRKSM                                              198

SEQ ID NO: 42            moltype = AA   length = 198
FEATURE                  Location/Qualifiers
source                   1..198
                         mol_type = protein
                         organism = Toxoplasma gondii
SEQUENCE: 42
MALSSLNNIR PFSGLLGCGL LFGALVVVVA CVFSVPVEAG VLRKVAGAGS LQASIGEHDF  60
FNDYDQDEEY RKRQQELQNQ SPEEVEEAKR KYHEELRRKA EEDAETKRKQ EAVIQELKEV 120
AKKRGLREAA EREEKRTDEQ QANYEQRQQE LRDMDSAMEE RLMQQRKKDQ EERELARKNS 180
DKVMEELKEK LARRRKSM                                              198

SEQ ID NO: 43            moltype = AA   length = 198
FEATURE                  Location/Qualifiers
source                   1..198
                         mol_type = protein
                         organism = Toxoplasma gondii
SEQUENCE: 43
MALSSLNNIR PFSGLLGCGL LFGALVVVVA CAFSVPVEAG VLRKVAGAGS LQASIGEHDF  60
FNDYDQDEEY RKRQQELQNQ SPEEVEEAKR KYHEELRRKA EEDAETKRKQ EAVIQELKEV 120
AKKRGLREAA EREEKRTDEQ QANYEQRQQE LRDMDSAMEE RLMQQRKKDQ EERELARKNS 180
DKVMEELKEK LARRRKSM                                              198

SEQ ID NO: 44            moltype = AA   length = 167
FEATURE                  Location/Qualifiers
source                   1..167
                         mol_type = protein
                         organism = Toxoplasma gondii
SEQUENCE: 44
MLVFLSAVFL QNGAFFFEQY QASIGEHDFF NDYDQDEEYR KRQQELQNQS PEEVEEAKRK  60
YHEELRRKAE EDAETKRKQE AVIQELKEVA KKRGLREAAE REEKRIDEQQ ANYEQRQQEL 120
RDMDSAMEER LMQQRKKDQE ERELARKNSD KVMEELKEKL ARRRKSM              167

SEQ ID NO: 45            moltype = AA   length = 198
FEATURE                  Location/Qualifiers
source                   1..198
                         mol_type = protein
                         organism = Toxoplasma gondii
SEQUENCE: 45
MALSSLNNIR PFSGLLGCGL LFGALVVVVA CVFSVPVEAG VLRKVAGAGS LQASIGEHDF  60
FNDYDQDEEY RKRQQELQNQ SPEEVEEAKR KYHEELRRKA EEDAETKRKQ EAVIQELKEV 120
AKKRGLREAA EREEKRIDEQ QANYEQRQQE LRDMDSAMEE RLMQQRKKDQ EERELARKNS 180
DKVMEELKEK LARRRKSM                                              198

SEQ ID NO: 46            moltype = AA   length = 198
FEATURE                  Location/Qualifiers
source                   1..198
                         mol_type = protein
                         organism = Toxoplasma gondii
SEQUENCE: 46
MALSSLNNIR PFSGLLGCGL LFGALVVVVA CVFSVPVEAG VLRKVAGAGS LQASIGEHDF  60
FNDYDQDEEY RKRQQELQNQ SPEEVEEAKR KYHEELRRKA EEDAETKRKQ EAVIQELKEV 120
AKKRGLREAA EREEKRIDEQ QANYEQRQQE LRDMDSAMEE RLMQQRKKDQ EERELARKNS 180
DKVMEELKEK LARRRKSM                                              198

SEQ ID NO: 47            moltype = AA   length = 198
FEATURE                  Location/Qualifiers
```

```
source                  1..198
                        mol_type = protein
                        organism = Toxoplasma gondii
SEQUENCE: 47
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 48           moltype = AA  length = 198
FEATURE                 Location/Qualifiers
source                  1..198
                        mol_type = protein
                        organism = Toxoplasma gondii
SEQUENCE: 48
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 49           moltype = AA  length = 198
FEATURE                 Location/Qualifiers
source                  1..198
                        mol_type = protein
                        organism = Toxoplasma gondii
SEQUENCE: 49
MALSSLNNIR PFSGLLGCGL LFGALVVVVA CVFSVPVEAG VLRKVAGAGS LQASIGEHDF    60
FNDYDQDEEY RKRQQELQNQ SPEEVEEAKR KYHEELRRKA EEDAETKRKQ EAVIQELKEV   120
AKKRGLREAA EREEKRIDEQ QANYEQRQQE LRDMDSAMEE RLMQQRKKDQ EERELARKNS   180
DKVMEELKEK LARRRKSM                                                 198

SEQ ID NO: 50           moltype = AA  length = 383
FEATURE                 Location/Qualifiers
source                  1..383
                        mol_type = protein
                        organism = Toxoplasma gondii
SEQUENCE: 50
MRGGTSALLH ALTFSGAVWM CTPAEALPIQ KSVQLGSFDK VVPSREVVSE SLAPSFAVTE    60
THSSVQSPSK QETQLCAISS EGKPCRNRQL HTDNGYFIGA SCPKSACCSK TMCGPGGCGE   120
FCSSNWIFCS SSLIYHPDKS YGGDCSCEKQ GHRCDKNAEC VENLDAGGGV HCKCKDGFVG   180
TGLTCSEDPC SKRGNAKCGP NGTCIVVDSV SYTCTCGDGE TLVNLPEGGQ GCKRTGCHAF   240
RENCSPGRCI DDASHENGYT CECPTGYSRE VTSKAEESCV EGVEVTLAEK CEKEFGISAS   300
SCKCDNGYSG SASATSHHGK GESGSEGSLS EKMNIVFKCP SGYHPRYHAH TVTCEKIKHF   360
ALDGAGNHDT TTYVARRRYP ASL                                           383

SEQ ID NO: 51           moltype = AA  length = 249
FEATURE                 Location/Qualifiers
source                  1..249
                        mol_type = protein
                        organism = Toxoplasma gondii
SEQUENCE: 51
YHPDKSYGGD CSCEKQGHRC DKNAECVENL DAGGGVHCKC KDGFVGTGLT CSEDPCSKRG    60
NAKCGPNGTC IVVDSVSYTC TCGDGETLVN LPEGGQGCKR TGCHAFRENC SPGRCIDDAS   120
HENGYTCECP TGYSREVTSK AEESCVEGVE VTLAEKCEKE FGISASSCKC DNGYSGSASA   180
TSHHGKGESG SEGSLSEKMN IVFKCPSGYH PRYHAHTVTC EKIKHFALDG AGNHDTTTYV   240
ARRRYPASL                                                           249

SEQ ID NO: 52           moltype = DNA  length = 3837
FEATURE                 Location/Qualifiers
source                  1..3837
                        mol_type = unassigned DNA
                        organism = Toxoplasma gondii
SEQUENCE: 52
tcttctcttc ttccgtactt ttccctgcat ttcacacccc tggtatgact ccacaccgcg    60
tgtaaatgtc ccttaggtga cacccgcagc agcgcgtagg aggaagtaga tgtcagtgta   120
gacgttttg agatgagaga cgataacgta aaatgccgcc gataacttct gcattataca   180
cactctctct ccacgcctag gatgacaggt acggcggcac acgaggaaaa gtggggggg   240
gggggggggc gaacagaaag gtcacatgga aggccgctcg actctccact cacgaagtga   300
aggcttcgtc ccgttttgct ggacaacgaa tgcgaactgc ttcactcgct tgtgacacac   360
acaactccag aggcacagag atgtgaagca gaagagtggc gtgtgcgtcg cttctgtcgg   420
cggcaagccc cgctccgtct cttttggtgg gattctggtg tgcaccgtgt gccaagaagt   480
tgcgtgtcac gcgacttttg gaaatgcatc aggttcagag tcgttatgtt gcgattcagg   540
ctctcggcag agaatcattt ccctgtaagc tagttgaact cgccttttta aaagcggcag   600
cagtgccctt gtggaaggcc tcactgtgcc tactttcctc gtcctgagtt tttccgcctt   660
cggcctcatt ttttgctcac caaaatcgtg tcctaccgtc aagttttgcc atagactcct   720
acgggaaaaa acaagccggt cgacacggac gacgcccgca gggaagcgtc cctccgcag   780
aaatcgggag acaactgtcg ttgacggtgc tgcgcgaaag gtcacagagt tccagtgtg   840
ttcatcgagc ctcactgtgc actgttacg gccgctgtcc cgcctggtca acaagtatca   900
cacctgtcgt ccgccattg gcacggagct cgatgagctg cagtgtcgct ttagggggag   960
```

-continued

```
tcgtgcaatc acgccgcaac acaggcgtga ttcgatcttc aattgctagg taaccactcg 1020
tgcttggtag ctctgcaatg gctcgagcga cggggggtgat gcaacatgct gctaaaaact 1080
cgacagacgt gtcaccggaa cccacctaaa taggagacca cgggtctctg gtgtgtcgcg 1140
tcgcattctc gcgtcgcatt ctcgcgtcgc aatgaccggc cagttgctcg acgtcgccag 1200
ccgggactga agagcgttca tcgagtcagc agcattgctc ccccttgctc ggtgaaaaaa 1260
gactctctgg tcgagtctag ctcgtgtcac ttctgtttct aacctccttc gttcaccggt 1320
acacctccga tgtgactttt ggtacacttg ccctgtcgca cgacgcacgc tgtcactcaa 1380
cttgctgcta gcgcaatcga taggttccct cgaaccagcc atcacacaca cacctttttcc 1440
gggaagacgt ttgcgggcgg tgggtcgcag ctcgtcgaga gtgcgttttct gtgcattttct 1500
gtgggcagtg cagcgcgttt gcgcgcctta tctctgtgt aacttccttg tccaacactg 1560
gtaaaaatgc gaggcgggac gtccgcgctg ttgcacgcgc tcaccttcag tggggccgtg 1620
tggatgtgca ccccagcgga ggctttgccg attcagaagt ctgtgcagct gggcagcttt 1680
gacaaagttg tgccgagccg cgaagtcgtc tctgagagtc ttgctccgtc tttcgcggtg 1740
actgagactc actcgtctgt gcaatccccc agcaagcagg acgcaact ctgtgctatc 1800
tcgagtgaag gcaagccatg tcgaaaccgt cagttgcaca ctgacaacgg gtacttcatc 1860
ggggccagtt gccccaagag cgcttgctgc agcaagacca tgtgcggccc cggcggctgc 1920
ggagaattct gctccagcaa ctggattttt tgcagcagtt cgctcatcta ccatcctgac 1980
aaaagctatg gaggagactg cagctgtgaa aagcagggcc atcggtgcga caaaaacgca 2040
gaatgcgtcg aaaacttgga cgcgggtggg ggtgtgcact gcaagtgcaa agacggcttc 2100
gtcggcactg ggttgacttg ctccgaggat ccttgttcaa aaagagggaa cgcgaagtgc 2160
ggacccaacg ggacgtgcat cgtcgtcgat tcagtcagct acacatgcac ctgcggcgac 2220
ggcgaaactc tagtgaacct ccccggaaggg ggacaaggat gcaagaggac tggatgtcat 2280
gccttcaggg agaactgcag ccctggtaga tgtattgatg acgcctcgca tgagaatggc 2340
tacacctgcg agtgccccac agggtactca cgtgaggtga cttccaaggc ggaggagtcg 2400
tgtgtggaag gagtcgaagt cacgctggct gagaaatgcg agaaggaatt cggcatcagc 2460
gcgtcatcct gcaaatgcga taacggatac tccggatacg cttccgcaac ctcccaccat 2520
gggaaaggag aatcgggatc cgaggggagc ttgagtgaaa aaatgaatat tgtcttcaag 2580
tgccccagtg gctaccatcc aagataccat gcccacaccg tgacgtgtga gaaaattaag 2640
cactttgccc ttgacggggc cggcaaccac gacacgacta cgtatgtcgc aagacgaagg 2700
tacccagcga gtctctgaga gcggagatca gcgcaaagac aagatgcgga gtttgactcg 2760
agaaacaata gtaacacgaa gtaaaaagtc tccacactaa gccaaggatt gagaatattt 2820
cgatttgtgc cgctggcaat agtggccttg gcctagaaag aagttctgca acgaagcgat 2880
cggctcacac gcggatacac agatgggttt gtaccgagaa cgttaggttt gtgaaccgag 2940
ttcaggtaaa acaaagtaga ttgtgccttt acgcagacag cgagggaaaa catgaggaca 3000
cactgccaac taaagcaaga ctgcctcact aattaccacc gacacacgac atggttaccc 3060
ccgcgttttg ccgcgtgcaa agtttgaatt ctgatggttc tcgagtctga aagcctaaac 3120
cgcccaacca tgtatgaaat aagaacccat caaacgtgag acatctctgc cgaagtgcct 3180
acgaaaagaa cgcttctgcc actaggaggt gcggcctctt cattctatga gaacctgctt 3240
tgtcggtgtc aacctctggg gaaatcgcct gcctttacac attttcgtcg ttgtagagca 3300
agggatctgt tgctgcgttt actccaatac aatgatcgcc gtttcgctgt aggcaagcga 3360
tccgaaaatg tacgttcgag tcagcagcta cttgagaagc agccaacgcc gacacttgct 3420
gcgtttgact gaggtgcact cgcaaacagt ctcgtctccc cggggcaatt tctgagagaa 3480
atgcggggaat ggacgtaatg gtgctcttct tgtgagtgctc ttccaccaat ttttcgacaa 3540
gtgttttcgt gacagtcgag tataccttct tatgtcattc tgtctccgtc agtgctatcg 3600
gattcttcct attcctctac cctttctaca gtcgcataca aagctgctga aacaagactt 3660
cctttgtcta gggtagttgt acactccaca catatctgac tgaaacctac ggcaggaagt 3720
ctggtcggca ctgtgcttcc ttgttggctt ttcgtcgttt ctttgtctac gagcttcact 3780
gggtccttga cacggccttg gagcgttgtg ctcaatattc gaccagctgt atttgtg    3837
```

SEQ ID NO: 53        moltype = DNA   length = 53
FEATURE              Location/Qualifiers
source               1..53
                       mol_type = unassigned DNA
                       organism = Toxoplasma gondii
SEQUENCE: 53
actgtggtct ctaggtatga tctaccatcc tgacaaaagc tatggaggag act           53

SEQ ID NO: 54        moltype = DNA   length = 39
FEATURE              Location/Qualifiers
source               1..39
                       mol_type = unassigned DNA
                       organism = Toxoplasma gondii
SEQUENCE: 54
acttgttcta gatcagagac tcgctgggta ccttcgtct                           39

SEQ ID NO: 55        moltype = AA    length = 580
FEATURE              Location/Qualifiers
source               1..580
                       mol_type = protein
                       organism = Toxoplasma gondii
SEQUENCE: 55

```
MRASLPVHLV VCTQLSAVWF GVAKAHGGHR LEPHVPGFLQ GFTDITPAGD DVSANVTSSE   60
PAKLDLSCVH SDNKGSRAPT IGEPVPDVSL EQCAAQCKAV DGCTHFTYND DSKMCHVKEG  120
KPDLYDLTGG KTASRSCDRS CFEQHVSYEG APDVMTAMVT SQSADCQAAC AADPSCEIFT  180
YNEHDQKCTF KGRGFSAFKE RGVLGVTSGP KQFCDEGGKL TQEEMEDQIS GCIQLSDVGS  240
MTADLEEPME ADSVGACMER CRCDGRCTHF TFNDNTRMCY LKGDKMQLYS SPGDRTGPKS  300
CDSSCFSNGV SYVDDPATDV ETVFEISHPI YCQVICAANP LCTVFQWYAS EAKCVVKRKG  360
FYKHRKTGVT GVTVGPREFC DFGGSIRDRE EADVGSDDG LNAEATMANS PDFHDEVECV  420
HTGNIGSKAQ TIGEVKRASS LSECRARCQA EKECSHYTYN VKSGLCYPKR GKPQFYKYLG  480
```

```
DMTGSRTCDT SCLRRGVDYS QGPEVGKPWY STLPTDCQVA CDAEDACLVF TWDSATSRCY    540
LIGSGFSAHR RNDVDGVVSG PYTFCDNGEN LQVLEAKDTE                          580

SEQ ID NO: 56           moltype = AA   length = 173
FEATURE                 Location/Qualifiers
source                  1..173
                        mol_type = protein
                        organism = Toxoplasma gondii
SEQUENCE: 56
SEPAKLDLSC VHSDNKGSRA PTIGEPVPDV SLEQCAAQCK AVDGCTHFTY NDDSKMCHVK    60
EGKPDLYDLT GGKTASRSCD RSCFEQHVSY EGAPDVMTAM VTSQSADCQA ACAADPSCEI    120
FTYNEHDQKC TFKGRGFSAF KERGVLGVTS GPKQFCDEGG KLTQEEMEDQ ISG           173

SEQ ID NO: 57           moltype = DNA   length = 3121
FEATURE                 Location/Qualifiers
source                  1..3121
                        mol_type = unassigned DNA
                        organism = Toxoplasma gondii
SEQUENCE: 57
ttttctgtgc atctgtgctg caaaacgggc ctctgtgcat tatttcccca ccaacaattg    60
ccgcgtcgat ccgggtcccg ctcaagctct gcagaactag gctctcgata tagatcagta    120
caatcattcg cttctgacaa tcgcatcgac tgagcgaccg gttgatcgtc gactgtcgtg    180
cgtcgcattc gggcatctcg aaccggtgtt gattccctgt gtcattattt cacttccgtc    240
cttctctcgt ggcgatctat aatacgcgtg tgttgttgcg tgcattgctt gtgttgttgt    300
ggatgtgttt tcttttgtga ccgctcacga acaccccacg caaatgagaa gcgtcgctcc    360
cggttcacct cgttgtgtgc acgcagctaa gtgccgtttg gtttggagtg gctaaagcct    420
atggtggaca ccgactggaa ccgcatgttc ccggattcct gcaaggcttc actgatatca    480
cgcctgcagg tgatgacgtt agtgccaacg taacaagttc ggagcctgca aaacttgatc    540
tctcttgtgt gcactctgac aataagggat caagggctcc cacaataggc gagccagtgc    600
cagatgtgtc cctggaacaa tgtgctgcgc aatgcaaagc tgttgatggc tgcacacatt    660
tcacttataa tgacgattcg aagatgtgcc atgtgaagga gggaaaaccc gatttatacg    720
atctcacagg aggcaaaaca gcatcgcgca gttgcgatag atcatgcttc gaacaacacg    780
tatcgtatga gggagctcct gacgtgatga cagcgatggt cacgagccag tcagcggact    840
gtcaggctgc gtgtgcggct gacccgagct gcgagatctt cacttataac gaacacgaa    900
agaaatgtac tttcaaagga aggggttttt ctgcgtttaa ggaacgaggg gtgttgggtg    960
tgacttccgg gccgaaacag ttctgcgatg aaggcggtaa attaactcaa gaggagatgg    1020
aagatcagat cagtggctgc attcaattga gtgacgttgg atcaatgact gctgacctgg    1080
aggagcctat ggaggctgat tctgttggcg cttgtatgga acggtgccgc tgtgatggaa    1140
gatgcacgca cttcacgttc aacgataata tcggatgtgt ctacctcaaa ggtgacaaga    1200
tgcagttgta ctcatctcca ggtgacagaa ccggcccaaa gagctgcgat tcaagctgct    1260
tctcgaacgg ggtttcttac gtcgatgatc cggcgacaga tgttgagacc gtattcgaaa    1320
tttcacaccc aatttattgt caagtaatct gcgccgcaaa tccgttgtgt acagtgtttc    1380
agtggtatgc ctccgaggca aagtgcgtcg tcaagagaaa ggggttttac aaacacagaa    1440
aaacaggtgt cacgggagtc acagtgggcc ctcgggagtt ctgcgatttt ggcggtagca    1500
tccgcgaccg agaagaggca gacgccgttg atcagacga tggcctcaac gcggaagcaa    1560
ctatggcaaa ttctcctgat tttcacgacg aagtagaatg cgtccacacg gcaacaattg    1620
ggtcaaaagc acaaaccatt ggagaagtga aacgcgcaag tagttttgagt gagtgcagag    1680
ccagatgcca agcggagaaa gaatgcagcc actacactta caatgtaaaa tccggtttgt    1740
gttatccaaa aagaggaaag cctcaatttt ataagtatct tggcgacatg acgggatcca    1800
gaacatgtga tacaagttgc cttaggaggg gagtcgatta ctcacaggc cctgaagtag    1860
gaaagccttg gtattctacg ctgccgacag actgccaagt tgcatgcgac gctgaggatg    1920
cttgcctggt gttcacctgg gattcggcga cgtcacgatg ctacctcatc ggctcaggtt    1980
tctcggcaca tcgacggaac gacgtggatg gcgtggtatc tggacccat ttttctgtg    2040
acaatgcgca aaaccttcag gtgcttgaag cgaaagacac agaatgaccc aggagggtgc    2100
cagatacttt gtgtgactgc gacatgcagt catgtactca aagtgttgta catggacagg    2160
aggactttt ttttaagtca ttgcagaggt gcgttttcgg agcagcacta taactgcgtc    2220
agcgactaag cacgccacgt agctgaatga aacgcagcca ccttcgtgta tgtatgcttc    2280
gttttttgtc gctgtgcagt tttgaatcat ttcccttatg ggacatttct gaaaatgct    2340
ccccgttcgc ttgtagcact atgagagggg ccgaagactg caatggaggt agcgctgcgt    2400
tgaaaagacg aggcgctaca tttcgcgtag cgacaaggcc gtgtagagtt ttgcttttcg    2460
cgagacactg ctctgagtgt catatgcatc aaatgcagtg gtagcacaca gaggtgagaa    2520
gaatgatcac ctgcggggga atggctttgc taaacaacaa ggtcgctgtg tgactttaca    2580
caacgaaact actgtggtga gtgctcagtt gagtgaaaag aaatgccgcg ttatcgtgag    2640
ttctggttcg gtggacttttg ccaccgtagt aaaactcaac ctgtaacgga atgccagttt    2700
ttactgctct cttttaaaggg cgtccacgtt ctctatattc aagctgttta cccacctgcg    2760
tttcggtgca tcgcgcgtgc cacataaaaa atccaggtaa cggtgcggga cctatgctac    2820
actttatatc tctcagaaag catacaccca ctgattatgg acaacgctgt ggtcgcgttg    2880
taccacaatg caggaatact cagttcacct tgcaagtgtt ctggtgttca ttgcgtgtca    2940
gaagtacacg aaaaagagact tctttggcct ccaagtgata cgtaaccgcg gcagtcagta    3000
acagagtcac tcgtgcttct gaaacgcacg tcttctgtac agagacagat gcagtgtgca    3060
tacaggaagc ccctcgattg ttgccgtagc aggtagccag tagaagaaac aaagacacgg    3120
t                                                                    3121

SEQ ID NO: 58           moltype = DNA   length = 54
FEATURE                 Location/Qualifiers
source                  1..54
                        mol_type = unassigned DNA
                        organism = Toxoplasma gondii
SEQUENCE: 58
```

```
actgtggtct ctaggtatga gttcggagcc tgcaaaactt gatctctctt gtgt        54

SEQ ID NO: 59          moltype = DNA   length = 47
FEATURE                Location/Qualifiers
source                 1..47
                       mol_type = unassigned DNA
                       organism = Toxoplasma gondii
SEQUENCE: 59
actgttctag atcagccact gatatgatct tccatctcct cttgagt                47

SEQ ID NO: 60          moltype = AA    length = 349
FEATURE                Location/Qualifiers
source                 1..349
                       mol_type = protein
                       organism = Toxoplasma gondii
SEQUENCE: 60
MRLFRCCAAA VVAAESLLWL KNGSPFFAFL PGNGEIADNC SGNPCGGTAA GTCINTPSGY   60
DCRCEPGYVL GVENDQVTCM MPSGVPMANF VQLSEKPAAC SSNPCGPEAA GTCNETNSGY  120
ICRCNQGYRI SLDGTGNVTC IVRQESGCEE NGCGPPDAVQ SCRRLTGTAG RLCVCKENFI  180
ATIDASAHIT CKRVPPHYRK PPFEFGKGGH PVDSEPSKRQ REDEGESREP ESDSTEPGRD  240
QERRTPLEES QEPEGSTPDS QQSRGGSGSD STESEEQGKE REEGSGHAGA IAGGVIGGLL  300
LLSAAGAGVA YMRKSGSGGG EEIEYERGIE AAEASEVEVL VDLDSKTWD             349

SEQ ID NO: 61          moltype = AA    length = 326
FEATURE                Location/Qualifiers
source                 1..326
                       mol_type = protein
                       organism = Toxoplasma gondii
SEQUENCE: 61
SPFFAFLPGN GEIADNCSGN PCGGTAAGTC INTPSGYDCR CEPGYVLGVE NDQVTCMMPS   60
GVPMANFVQL SEKPAACSSN PCGPEAAGTC NETNSGYICR CNQGYRISLD GTGNVTCIVR  120
QESGCEENGC GPPDAVQSCR RLTGTAGRLC VCKENFIATI DASAHITCKR VPPHYRKPPF  180
EFGKGGHPVD SEPSKRQRED EGESREPESD STEPGRDQER RTPLEESQEP EGSTPDSQQS  240
RGGSGSDSTE SEEQGKEREE GSGHAGAIAG GVIGGLLLLS AAGAGVAYMR KSGSGGGEEI  300
EYERGIEAAE ASEVEVLVDL DSKTWD                                      326

SEQ ID NO: 62          moltype = DNA   length = 3394
FEATURE                Location/Qualifiers
source                 1..3394
                       mol_type = unassigned DNA
                       organism = Toxoplasma gondii
SEQUENCE: 62
cagtccggag cacactccta caataaactt gatacgtgtc attttgtgaa acgacacagc   60
acataaccac tcggactgtc tcacgaagct gtagggcgga ttcaccaatg atctttcgca  120
gccgatccaa aactacttgc ccacttccgg tgtacgtaca tcgcgcgaca tgagaggcat  180
tcattgtttt ccatagaaaa cactactgga caaccattcg gtagcgcaca agttgagcct  240
ctgacaaatc tttcctcatc acgtgaatac acgctgcagt attcgtcagt gactccactg  300
tggtctttaa ccaccatcag agtcctgtaa gcatccttg tttccgttta aaatgcctgc  360
cagatggcac gacgccgtct ggttttgccg gctttctccg agtcctatta gacttttgatg  420
ccttacggct ttttttaag aatggttctt ttgagatttg ccgactttcc agttccgcca  480
ccagacgctc ctgttgaact gccaccggca cgatgcagta ttccgccacg aaaacgcgca  540
ccgcaagctc cgctaccatt aaacgggttt cgtctgcttt agatgttttcc ttccgcgtca  600
tcaaggcaaa agcattgcca ctgatgttac cgaagctttc ccgccatgct gcgcacaatg  660
cccaatcttc cgtcacggac tcttccggt aaccacctaa aggaggatta ctgggcaacc  720
caaaacgctg caacaagaag cacagtccag gtgtcgctag attcgagcct gcatggtcgt  780
tccgtagctc catacaacaa ttctctgtgt gacggcgaga ggagtaacgc gctagtcgta  840
gtcagcgacg cggcagtcga tccgatcctg caacaggcag aggtgtgtcg atgctcagtg  900
atgcgacggc gtatctgaag aggactgtag ctccaccacg accttcgtgg gagcacgaag  960
tgtactctgt tgtcgtcggt ctcgtatttt tttgagtttg gtacttcgct gcaagaggag 1020
ggtgagattc gacatctgtg ggcgtttggg atcgtgatga catcgactgt gctttgatat 1080
atgatgtgtt tttttttcgat tggatgagca cattccagta agcttcctgc cgcgcgtctc 1140
tgctatgagg ctcttccggt gctgtgctgc ggccgttgtg gcggccgaat cgttactgtg 1200
gctgaagaac ggctccccgt ttttttgcctt tcttcctggg aatggagaga ttgcagacaa 1260
ctgctctggg aatccatgcg gtggcaccgc agctggtacg tcataaaca caccatctgg 1320
atatgattgc aggtgcgaac caggctacgt tctgggcgtt gaaaatgacc aggtcacgtg 1380
catgatgccc tcaggtgtac ccatggctaa ttttgtacag ctgtcggaaa agcctgcagc 1440
ttgcagctca aaccccttgtg gacctgaggc agccggcacc tgcaacgaga caaacagtgg 1500
ttacatttgc cgctgtaatc aaggctacag aatatctctc gacgggacga gaaacgtgac 1560
atgtattgta agacaggaaa gcggctgtga ggaaacggg tgggtgccgc cagatgcgat 1620
acagagttgc cgccgactaa cagggacggc aggtcgacta tgtgtatgca aggaaaactt 1680
tatagcgaca atcgacgcca gtgcccatat cacctgcaag cgtgtgcctc cccattatag 1740
gaagcctccc ttcgaatttg gcaagggagg tcatcctgtg gactcagaac catcgaaacg 1800
ccagagggaa gatgaaggtg aaagtcgtga gcctgaaagc gactcaacag aaccgggaag 1860
agatcggaa agaagaacac cacttgagga aagccagaag gacccccgaa 1920
cagtcagcag agccgaggtg gttctgctag cgacagtacc gagagcgagg aacaaggaaa 1980
ggagagagag gaaggaagtg gacatgctgg tgcgatcgct gggggagtta ttggaggcct 2040
gttacttctg agcgctgccg gagcgggtgt tgcatacatg agaaagagtg ggagcggtgg 2100
agggagggag atagaatacg agaggggtat cgaggctgca gaggccagtg aagtcgaagt 2160
cctcgttgat ttggatagca aaacatggga ttaacacgtt ctcggctgag acttcacaat 2220
```

```
gtagggtgtc gctggcagat cagctgcaat gcgagaggtg acgcgagtag tgagcaccgc   2280
ttcttttaag cgcggacatt gtgctcggtc ttctgtcacc cccgaatcaa aacacatgta   2340
tgataatagt tcctgttgac ttcccctgcc gacaaagaac tgctgtgtcg aggccggctt   2400
ctgtgcactc atcccaaatg agatggactg atgttttaga gacacctcat cgccgacgga   2460
aaccatcagc tcccagagaa actatgctgc gtcgtttttt aggtgatctg ttgcgtaatg   2520
cgcaccttca tatcatctgt gtgttgactg tttggtcgtt ttccgtttag tcaaatgaat   2580
gcagtgaaat gcagggaatt tagcagacac cgagaactgt cctcttgttc tgtgcgcgag   2640
ttgtttttaa cgtatagcga tgcgtttgca cttgatatta ccctaagcca tcagtgggta   2700
tttagaggag cccacaggtg atgggggtga tccctgtttc ttgtcatttg gcttgtaggg   2760
ttcgctggaa ctatctggtg tcacggaaga gtggctttac tgtctgtccc caaacgcaag   2820
gcatcagtgt aaccccgata ggactctgga gacttctgct tcactgccgc gttgcaattt   2880
tcccgcgtca tgtggcaata acggtaattc cacgtgcacg ccgcataccg gatctttgct   2940
cccaggcttt cttatgaggt cggcatacgt acagcggcgg cgtacctccg ctctagaaa    3000
gaccggtcca accgactttg aacagcatgc ttgtgaatga gtgcttaaac accctgaagt   3060
gatggtggaa tgtagcagtc tgggacggtt gatgcgagga tatcaccatt agcatagact   3120
accttgctct ttagcgaggc gagacaactt atttaggtag ccatgaaaca cctcgatagt   3180
atcaatgacg acgtgcggtt caccaacttc cgtcgctagc gcagaaaaca gtcggaaaca   3240
caactcggtg agcacctgaa gtgtcagtac acattcgacc gtcgggaccc gggattccgc   3300
aagtggcacc cgctggtcca gtagcaggaa cctagttcat tcagtataac agatttgggg   3360
cggcaaagag caatttgctc gacctaacgc ttgc                               3394

SEQ ID NO: 63          moltype = DNA  length = 44
FEATURE                Location/Qualifiers
source                 1..44
                       mol_type = unassigned DNA
                       organism = Toxoplasma gondii
SEQUENCE: 63
actgtgtgct ctaggtatgt ccccgttttt tgcctttctt cctg                    44

SEQ ID NO: 64          moltype = DNA  length = 39
FEATURE                Location/Qualifiers
source                 1..39
                       mol_type = unassigned DNA
                       organism = Toxoplasma gondii
SEQUENCE: 64
actgttctag attaatccca tgttttgcta tccaaatca                          39
```

ANTIGENS FOR DETECTING TOXOPLASMA INFECTION BY MONITORING CELLULAR IMMUNITY

TECHNICAL FIELD OF THE INVENTION

This invention is related to the area of clinical testing. In particular, it relates to cellular immune responses including delayed type hypersensitivity reactions and cytokine release, or interferon gamma secretion assays, and their use in diagnosis of toxoplasmosis.

REFERENCE TO A SEQUENCE LISTING

This application contains a Sequence Listing that has been submitted in ASCII format via Patent Center and is hereby incorporated by reference in its entirety. The ASCII copy, created Sep. 8, 2023, is named "016695_US_DIV2", and is 85.500 bytes in size.

BACKGROUND OF THE INVENTION

In *Toxoplasma gondii*, there are three main compartments, called dense granules (GRA proteins), rhoptries (ROP), and micronemes (MIC proteins), which release antigens into the extracellular milieu (Carruthers V B, Sibley L D. 1997. *Sequential protein secretion from three distinct organelles of Toxoplasma gondii accompanies invasion of human fibroblasts*. Eur J Cell Biol 73:114-123). Although both GRA and MIC compartments release antigens constitutively at low levels, micronemes can be stimulated to release large amounts of antigen in response to certain environmental cues, such as contact with host cells or other host factors (Carruthers V B, Giddings O K, Sibley L D. 1999. *Secretion of micronemal proteins is associated with Toxoplasma invasion of host cells*. Cell Microbiol 1:225-236; Carruthers V B, Sibley L D. 1997. *Sequential protein secretion from three distinct organelles of Toxoplasma gondii accompanies invasion of human fibroblasts*. Eur J Cell Biol 73:114-123; Carruthers V B, Sibley L D. 1999. *Mobilization of intracellular calcium stimulates microneme discharge in Toxoplasma gondii*. Mol Microbiol 31:421-428). Collectively, proteins that are released either constitutively or in a regulated fashion have been defined as "excretory secretory antigens (ESA)."

The ESA fraction is enriched in secretory microneme (MIC) proteins but also contains constitutively secreted dense granule (GRA) proteins. Several MIC and GRA proteins have been described. Previous studies have shown that MIC2, and its binding partner MIC2 associated protein (M2AP), are abundant components of ESA (Huynh M H, Barenau K E, Harper J M, Beatty W L, Sibley L D, Carruthers V B. 2003. *Rapid invasion of host cells by Toxoplasma requires secretion of the MIC2-M2AP adhesive protein complex*. EMBO J 22:2082-2090). Additionally, MIC5 (Brydges S D, Sherman G D, Nockemann S, Loyens A, Daubener W, Dubremetz J, Carruthers V B. 2000. *Molecular characterization of TgMIC5, a proteolytically processed antigen secreted from the micronemes of Toxoplasma gondii*. Mol Biochem Parasitol 111:51-66) and MIC10 (Hoff E F, Cook S H, Sherman G D, Harper J M, Ferguson D J, Dubremetz J F, Carruthers V B. 2001. *Toxoplasma gondii: molecular cloning and characterization of a novel 18-kDa secretory antigen, TgMIC10*. Exp Parasitol 97:77-88) have been studied as soluble micronemal proteins that are immunogenic. Several MIC proteins interact: for example MIC1, MIC4 and MIC6 form a complex involved in recognition of host carbohydrates (Friedrich N, Santos J M, Liu Y, Palma A S, Leon E, Saouros S, Kiso M, Blackman M J, Matthews S, Feizi T, Soldati-Favre D. J Biol Chem. 2010 285:2064-76, Blumenschein T M, Friedrich N, Childs R A, Saouros S, Carpenter E P, Campanero-Rhodes M A, Simpson P, Chai W, Koutroukides T, Blackman M J, Feizi T, Soldati-Favre D, Matthews S. EMBO J. 2007 26:2808-20) Gene deletions of MIC1 or MIC3 alone do not have a profound effect on invasion, but the double mutant is attenuated, indicating these proteins plan complementary roles (Moiré N, Dion S, Lebrun M, Dubremetz J F, Dimier-Poisson I. Exp Parasitol. 2009 123:111-7). MIC1 has been used in a variety of immunodiagnostic assays based on detection of antibodies that react to this protein (Holec L, Gasior A, Brillowska-Dabrowska A, Kur J. Exp Parasitol. 2008 119:1-6) or to hybrid proteins containing MIC1 and other parasite antigens (Holec-Gasior L, Ferra B, Drapala D. Clin Vaccine Immunol. 2012 19:1977-9). As well, MIC1 and MIC4 have been used in vaccination studies in mice (Lourenco E V, Bernardes E S, Silva N M, Mineo J R, Panunto-Castelo A, Roque-Barreira M C. Microbes Infect. 2006 8:1244-51). Other studies have shown that the secretory proteins GRA4, GRA6, and GRA7 are targets of the immune response (Mercier C, Cesbron-Delauw M F. 2015. *Toxoplasma secretory granules: one population or more?* Trends Parasitol 31:60-71).

Delayed type hypersensitivity (DTH) responses are driven by cellular immune responses to antigens (Black C A. 1999. *Delayed type hypersensitivity: current theories with an historic perspective*. Dermatol Online J 5:7). Typically a test antigen is injected in the skin of the ear, flank, or footpad and swelling measured 24-48 hr later (Allen I C. 2013. *Delayed-type hypersensitivity models in mice*. Methods Mol Biol 1031:101-107). The most well-known test uses tuberculin, an extract of purified protein derivative (PPD) from mycobacteria, which is used in a skin test for tuberculosis infection. The skin test is also the basis for many allergy testing protocols. Although previous studies have used skin testing of toxoplasmin in mice and hamsters based on swelling and redness, these assays have not proven to be that specific or sensitive (Frenkel J K. 1948. *Dermal hypersensitivity to toxoplasma antigens (toxoplasmins)*. Proc Soc Exp Biol Med 68:634-639). Previous studies testing toxoplasmin, a skin test reaction elicited by ESA antigens, showed that it was sensitive and specific for detecting individuals in France that were chronically infected with *T. gondii* (Rougier D, Ambroise-Thomas P. 1985. *Detection of toxoplasmic immunity by multipuncture skin test with excretory-secretory antigen*. Lancet 2:121-123). In those studies, the ES antigen was made from culture supernatants, fixed with formalin, and then dialyzed with a 10 kDa filtration step. In subsequent studies, others have indicated that the active component in toxoplasmin is in the range of 10 kDa to 50 kDa based on filtration (Veprekova. 1978. *Approximative molecular weight of the active component in toxoplasmin*. Folia Parasitol (Praha) 25:273-275). It should be noted that proteins may undergo proteolytic processing or breakdown, so this size range does not necessarily indicate the size or identity of the full-length protein. Although these studies refined our knowledge of the active components of ESA, the active components remain undefined at the molecular level. Moreover, there is no way to produce the ESA fraction in large quantities such that it could be made into a commercial product.

Delayed type hypersensitivity reactions are predominately driven by CD4+ memory T cells that recognize antigen from a previous exposure (*Mantoux Test as a model*

*for a secondary immune response in humans.* Vukmanovic-Stejic M, Reed J R, Lacy K E, Rustin M H, Akbar A N. Immunol Lett. 2006 10793-101). Upon recognition of their cognate antigen, these memory T cells expand and produce cytokines including interferon gamma (IFN-γ) tumor necrosis factor (TNF) and other chemokines. This initial reaction also results in recruitment of mononuclear (i.e. monocytes) cells and polymorphonuclear (i.e. PMNs) cells from circulation into the tissue. Although the conventional DTH test relies on monitoring induration, and redness that develop at the site of injection, more recent tests have been developed to directly monitor T cells responses to specific antigens. Typically these responses are monitored in circulating T cells obtained from the leukocyte fraction of whole blood. Leukocytes, including antigen-presenting cells and T cells, are mixed in vitro with antigens and the resulting responses monitored by production of IFN-γ or other cytokines. In some applications there are referred to as INFγ-release or IFN-γ-secretion assays, owing the fact that IFN-γ is the primary cytokine thought to drive the DTH response. The advantages of such tests is that they are more quantitative than the traditional skin test, they can be completed with a single office visit, and they often suffer less from cross-reaction to environmental antigens.

The enzyme-linked immunospot or ELISpot assay was originally developed for detecting B cells that were secreting antigen-specific antibodies (*A solid phase immunoenzymatic technique for the enumeration of specific antibody-secreting cells.* Sedgwick J D, Holt P G. J Immunol Methods. 1983 February 57:301-9). It has seen been modified to detect cytokines secreted by different immune cells. The principle of the assay is that it relies on a sandwich ELISA where a membrane-backed microplate (typically polyvinylidene difluoride) is coated with antibodies to a particular cytokine. Cells from healthy or immune donors are added the plate and incubated overnight in medium under standard culture conditions. Cytokines secreted during this incubation are captured by the antibody-coated membrane. Following the incubation period, the cells are washed off and the captured cytokine is detected by a second antibody that is specific for the protein of interest. Detection is accomplished using an enzyme-linked reagent, either secondary antibody, or streptavidin to detect the biotinylated primary antibody.

ELISpot assays have previously been used for detection of IFN-γ secretion by T cells in patients that were chronically infected with *Toxoplasma gondii* (*Evolving characteristics of toxoplasmosis in patients infected with human immunodeficiency virus*-1*: clinical course and Toxoplasma gondii-specific immune responses.* Hoffmann C, Ernst M, Meyer P, Wolf E, Rosenkranz T, Plettenberg A, Stoehr A, Horst H A, Marienfeld K, Lange C. Clin Microbiol Infect. 2007 13:510-5). This study focused on immunocompromised patients and used the ELISpot assay as a surrogate for CD4+ T cell responses to whole antigen. Although this study did not evaluate the ELISpot assay as a primary diagnostic tool, it suggests that the degree of immunity in a patient can be inferred from the strength of the response in the ELISpot assay. In this case the ELISpot test was conducted with whole parasite antigen and no attempt was made to define useful antigens that would increase sensitivity or specificity using this assay.

SUMMARY OF THE INVENTION

According to one aspect of the invention, a *Toxoplasma gondii*-derived antigen composition is provided. The composition comprises a *Toxoplasma gondii*-derived antigen selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may alternatively or additionally comprise or consist of any of the antigens shown in Table 1.

According to another aspect of the invention, a kit is provided. The kit comprises (a) a *Toxoplasma gondii*-derived antigen composition and (b) an applicator device for administration of the *Toxoplasma gondii*-derived antigen to a subject. The composition comprises a *Toxoplasma gondii*-derived antigen selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

According to yet another aspect of the invention a method of delivering *Toxoplasma gondii*-derived antigen to a subject is provided. An applicator device that is loaded with a *Toxoplasma gondii*-derived antigen composition is contacted with skin of the subject. The *Toxoplasma gondii*-derived antigen composition is thereby delivered to the skin of the subject. The composition comprises a *Toxoplasma gondii*-derived antigen selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

Yet another aspect of the invention is an applicator device for administering one or more *Toxoplasma gondii*-derived antigens to a mammal. The applicator device comprises one or more *Toxoplasma gondii*-derived antigens. The *Toxoplasma gondii*-derived antigens are selected from the group consisting of: isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

Yet another aspect of the invention is a method of eliciting and/or monitoring a T cell response in a subject. A *Toxoplasma gondii*-derived antigen composition is contacted with T cells of the subject. The *Toxoplasma gondii*-derived antigen composition induces a T cell response, which may involve production or secretion of cytokines. The *Toxoplasma gondii*-derived antigen composition may be isolated and purified MIC1, MIC3, MIC4, or MIC6; truncated MIC1, MIC3, MIC4, or MIC6; extended MIC1, MIC3, MIC4, or MIC6; a fusion protein comprising any two or more of MIC1, MIC3, MIC4, or MIC6; a fusion protein of any of MIC1, MIC3, MIC4, or MIC6 with a moiety that enhances or facilitates purification, recombinant production, or immune cell stimulation, and combinations thereof as elements of an antigen or components of a composition. The *Toxoplasma gondii*-derived antigen composition may comprise or consist of any of the antigens shown in Table 1.

These and other embodiments which will be apparent to those of skill in the art upon reading the specification provide the art with

BRIEF DESCRIPTION OF THE DRAWINGS

The patent or application file contains at least one drawing executed in color. Copies of this patent or patent application with color drawing(s) will be provided by the Office by request and payment of the necessary fee.

FIG. 3A) Animals were injected with antigens in The ear pinne. At 48 hr after injection, animals were imaged after injection of luminol using a Xenogen IVIS 200 instrument. Animals were injected with either ESA or total antigen. Numbers indicate antigen amounts in micrograms. FIG. 3B) Quantification of the images shown in A. Data were processed using Living Image software.

FIG. 6A) Responses from C57/BL6 mice, FIG. 6B) Responses from Balb/C mice. Individual data points represent a result from one mouse, either uninfected (gray) or chronically infected (black). SFC indicates "spot forming cells" that were positive for INFγ secretion.

DETAILED DESCRIPTION OF THE INVENTION

Figure 1:
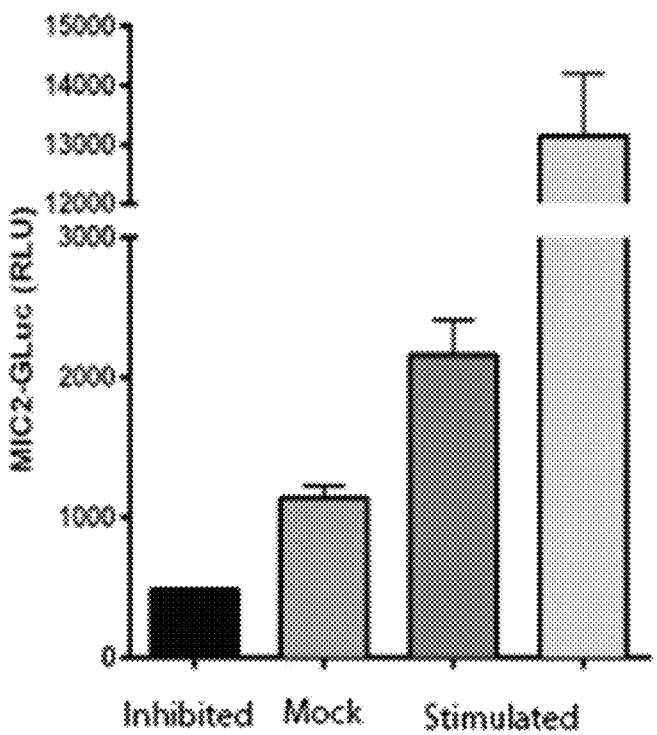
FIG. 1 shows a luciferase-based secretion assay. Secretion was monitored by release of the reporter protein MIC1-GLuc into the supernatant. Samples include cells that were treated with BAPTA-AM to block secretion (Inhibitor), cells treated only with buffer (Mock), and cells treated with BSA and zaparinast (Stimulated). These later samples contain the fraction that is referred to as ESA.

The inventors have developed a standardized, abundant test antigen composition for use in sensitively and specifically testing individuals for infection by *Toxoplasma gondii*. Antigens that cause a non-specific reaction (whether the subject has been infected or not) and antigens that cause a specific reaction (only in subject that has been infected) have been identified. The latter have been purified and cloned and modified to form test reagents. The former have been eliminated from test reagents.

The compositions of antigens preferably contain only antigens that cause a specific reaction and are devoid of antigens that cause a non-specific reaction. Such preparation may be made by any means known in the art, including isolation and purification from, e.g., natural sources, recombinant production, or synthetic production. Carriers for the antigens may be any standardly used, typically a carrier that does not itself cause a DTH reaction or inhibit a DTH reaction by a bona fide antigen. Non-limiting examples of excipients that may be used for the antigen compositions are sucrose, mannitol, trehalose, and Hemaccel™ (intravenous colloid). Buffers, salts, sugars, preservatives, isotonic saline solutions, phosphate-buffered saline, can also be used in the compositions. Additional components and excipients include water, polymers, fatty acid esters, parabens. Compositions may be stored as convenient, including without limitation as lyophilized samples, at about or below 4 degrees C., and at about or below −70 degrees C.

Compositions of antigens may be free of other ESA components such as dense granular proteins (GRA), other microneme proteins, or other components which lead to lower sensitivity and/or specificity. An isolated and purified preparation may be from *T. gondii* organisms, from a recombinant host cell, or from a synthetic in vitro reaction. The isolated and purified protein may comprise at least at least 1%, at least 5%, 10%, at least 20%, at least 25%, at least 30%, at least 40%, at least 50%, at least 60%, at least 70%, at least 75%, at least 80%, at least 85%, at least 90%, at least 95%, at least 97%, or at least 99% of the protein in a composition.

Testing for DTH may be used in order to prevent or detect congenital toxoplasmosis, for example by testing women before or during pregnancy, respectively. Primary infection of pregnant women may lead to abortion or severe neonatal malformation. Testing may also be used in immunocompromised patients, in whom a severe form of the disease may be fatal. Testing for DTH might also be performed in healthy adults to determine their infectious status prior to performing a medical procedure as a consequence of which they may become immunocompromised. Detection of infection may be critical in managing the disease. If a positive DTH test occurs, it may be desirable to follow it with a serum test. Because the two types of tests detect different immunological pathways and components, the two types of tests may give complementary information. Serum tests detect antibodies, whereas DTH tests detect cellular immune responses.

As an alternative, an in vitro reaction may be used to detect a T cell response. The in vitro reaction may be performed on any source of T cells, including whole blood, serum, plasma, and other tissue sources of T cells. The T cells are contacted with one or more of the *Toxoplasma gondii*-derived antigens or an antigen composition. If the T cells are reactive with the antigens or antigen composition they release a cytokine such as interferon-γ or other cytokines. The presence of interferon-γ or other released cytokine can be detected using any technique known in the art, including but not limited to an antibody or a series of antibodies. The antibodies may be labeled for detection. An antibody may be attached to an enzyme, such as horseradish peroxidase or alkaline phosphatase that produces colored products in the presence of appropriate substrates. An antibody may be fluorescently labeled, as an alternative. The in vitro reaction product may be captured on a solid support or assayed in the reaction fluid.

Kits may comprise an outer package to contain all components as well as optional inner packaging to contain individual components or combinations of components. Optional components include instructions for assembly and/or administration, information on side effects, expiry information, etc. Information may be provided in paper form, on a digital medium, or as an internet address to such information.

Applicators may be any type as is known in the art for administering an antigen to the skin of a subject and developing a DTH response. These include without limitation patches, needles, multi-needle assemblies, prongs, multi-prong assemblies. Antigens may be administered individually at separate locations or in combination at a single location.

Fusion proteins can be made using recombinant DNA technology to express two or more proteins or polypeptide portions of proteins as a single expression product. Any suitable technique known in the art for making and expressing such fusion proteins may be used. In some embodiments, a non-*T. gondii* protein is fused to a *T. gondii* protein. In other embodiments, two distinct *T. gondii* proteins are fused together.

Amounts of antigen composition that may be administered can be empirically determined, but may be between 0.1 and 50 ug, between 0.5 and 25 ug, or between 1 and 10 ug.

Suitable subjects include, but are not limited to, a human, a livestock animal, a companion animal, a lab animal, and a zoological animal. A subject may or may not be known to have a TDP43-mediated disorder. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

MIC1 is normally a 456 residue (amino acid) protein that is processed in the parasite remove the N-terminal 16 residues. This leaves a total size of 440 residues. In contrast to this native protein, the form we have expressed, termed here truncated MIC1, is from residues 20-340, for a total size of 320 amino acids. This region of the protein contains a micronemal adhesive repeat that has been shown to bind to host sialic acid residues [Garnett, J. A., et al., *Detailed insights from microarray and crystallographic studies into carbohydrate recognition by microneme protein 1 (MIC1) of Toxoplasma gondii*. Protein Sci, 2009. 18(9): p. 1935-47.]. We expressed a truncated version of the protein in order to make it soluble, a property that would distinguish it from the native molecule that also contains a C-terminal galectin domain [Saouros, S., et al., *A novel galectin-like domain from Toxoplasma gondii micronemal protein 1 assists the folding, assembly, and transport of a cell adhesion complex*. J Biol Chem, 2005. 280(46): p. 38583-91.]. It may, as a result, be recognized differently by the immune system.

MIC3 is normally a 383 residue (amino acids) protein that is processed in the parasite to remove the N-terminal 26 residues. This leaves a mature protein of 357 residues. We expressed a truncated form of MIC3 from residues 134 to 383, for a total size of 250 residues. We expressed a truncated version of the protein in order to make it soluble, a property that distinguishes it from the native molecule. The truncated form of MIC3 lacks most of the N-terminal lectin domain (residues 67-145) but contains the EGF repeats (residues 145-359) described previously (*The Toxoplasma gondii protein MIC3 requires pro-peptide cleavage and dimerization to function as adhesin*. Cérède O, Dubremetz J F, Bout D, Lebrun M. EMBO J. 2002 21:2526-36).

MIC4 is normally a 580 residue (amino acid) protein that is processed in the parasite to remove the N-terminal 25 amino acids. This leaves a mature protein of 555 amino acids. Biochemical studies have shown that the full length protein is further processed at the N-terminus between residues 57-58 (VT-SS) and by a C-terminal processing event to generate a 50 kDa and a 15 kDa products (*The toxoplasma micronemal protein MIC4 is an adhesin composed of six conserved apple domains*. Brecht S, Carruthers V B, Ferguson D J, Giddings O K, Wang G, Jakle U, Harper J M, Sibley L D, Soldati D. J Biol Chem. 2001 276:4119-27). We expressed a truncated form of MIC4 from residues 58 to 231, for a total size of 173 residues, a property that distinguishes it from the native molecule. The region of the protein that we expressed contains the first two Apple domains, but lacks the C-terminal Apple domains 5,6 that mediate binding to host cells (*The toxoplasma micronemal protein MIC4 is an adhesin composed of six conserved apple domains*. Brecht S, Carruthers V B, Ferguson D J, Giddings O K, Wang G, Jakle U, Harper J M, Sibley L D, Soldati D. J Biol Chem. 2001 276:4119-27).

MIC6 is a 349 residue (amino acid) protein that is processed in the parasite to remove the first 23 residues. This leaves a mature protein of 326 residues that was expressed as a recombinant protein in *E. coli*. This full-length form of the protein contains three EGF domains, a single acidic domain and a transmembrane domain near the C-terminus as described previously (*Structural insights into microneme protein assembly reveal a new mode of EGF domain recognition*. Sawmynaden K, Saouros S, Friedrich N, Marchant J, Simpson P, Bleijlevens B, Blackman M J, Soldati-Favre D, Matthews S. EMBO Rep. 2008 9:1149-55).

The mixture of ESA proteins, previously referred to as useful for a human skin test [Rougier, D. and P. Ambroise-Thomas, *Detection of toxoplasmic immunity by multipuncture skin test with excretory-secretory antigen*. Lancet, 1985. 2(8447): p. 121-3] may contain proteins that elicit non-specific responses. By removing these contaminants and focusing on proteins that only give positive responses in infected animals (and individuals) including MIC1, MIC3, MIC4, and MIC6, and truncated and/or fused forms of these proteins, our test achieves properties that are superior to the natural mixture of ESA proteins.

Previous studies have identified short peptide residues that enhance uptake by dendritic cells and increase the efficiency of antigen presentation [Sioud, M., et al., *A novel peptide carrier for efficient targeting of antigens and nucleic acids to dendritic cells*. FASEB J, 2013. 27(8): p. 3272-83.]. The receptor to which these peptides bind on host dendritic cells is not known. Nonetheless, it is likely that these short sequences work by enhancing uptake of the antigen and priming the presentation pathway. These steps of antigen uptake, processing, and presentation are critical for the DTH response. MIC1, MIC3, MIC4, and MIC6 and truncated and/or fused forms of these proteins, can be expressed so that these sequences are either at the N- or C-termini. These modified antigens can be purified under conditions that minimize contamination with LPS. Levels of LPS may be reduced to less than 0.5 EU/ml, less than 0.25 EU/ml, less than 0.1 EU/ml, less than 0.05 EU/ml. Any modification described herein for MIC1, 3, 4, or 6 can also be applied to any of the proteins of Table 1 or Table 2.

The above disclosure generally describes the present invention. All references disclosed herein are expressly incorporated by reference. A more complete understanding can be obtained by reference to the following specific examples that are provided herein for purposes of illustration only, and are not intended to limit the scope of the invention.

EXAMPLES

Example 1

Stimulation of Microneme Secretion

Freshly isolated tachyzoites of *Toxoplasma gondii* were stimulated to secrete Excretory-Secretory Antigens (ESA) using procedures similar to those published previously [1]. In brief, high-binding 96-well plates were coated with 1% bovine serum albumin (BSA) in phosphate buffered saline (PBS) pH 7.4 or PBS alone at 4° C. overnight. The next day, plates were washed with PBS to remove soluble BSA just prior to the secretion assay. Freshly harvested type I strain RH-parasites were purified and resuspended in intracellular buffer (25 mM HEPES pH 7.4, 142 mM KCl, 5 mM NaCl, 1 mM $MgCl_2$, 2 mM EGTA, 5.6 mM D-Glucose). Control parasites were treated with 50 μM BAPTA-AM to suppress secretion and added to wells washed with PBS (no BSA coating). For stimulated samples, untreated parasites were added to BSA-coated wells in the presence of 500 μM zaprinast. Parasites were allowed to secrete for 10 min at 37° C. prior to collection of the supernatant. Duplicate samples for each treatment were processed for liquid chromatography and tandem mass spectrometry (LC/MS-MS).

Identification of *Toxoplasma*-Secreted Proteins in ESA by LC-MS/MS

Secreted proteins were detected by LC-MS/MS as previously described [1]. In brief, ESA samples were reduced with 10 mM Tris-(2-carboxyethyl)phosphine and alkylated with 20 mM iodoacetamide before digestion overnight with 0.5 ug of trypsin. After desalting, the digest was then dried down and resuspended in 15 μl of 5% acetonitrile, 0.1% formic acid. Five microliters was resolved by LC-MS/MS on a NanoLC Ultra (Eksigent Technologies) coupled with an LTQ-Velos Pro Orbitrap (Thermo Scientific) using a 2 hr gradient. Raw data were processed and compared to the predicted proteome of the *T. gondii* genome to identify the protein components of ESA, as described previously [2]. For comparative semi-quantitative analysis, fold-enrichment was calculated from the frequency of spectral counts for peptides in the BSA-zaprinast stimulated samples compared to the BAPTA-AM treated control (set at 1 where no peptides were detected) for each protein detected in ESA. Proteins were considered candidate ESA proteins if the average fold enrichment was ≥4 in both of two independent experiments. Additionally, the cell-cycle specific expression profile for each candidate gene was analyzed to determine if it matched the profile of known microneme protein encoding genes [3]. Only proteins that fit both criteria (4 fold enriched and micronemal transcriptional profile) were considered authentic ESA-enriched proteins.

Cloning and Expression of *T. gondii* Antigens

Gene sequences encoding *T. gondii* microneme (MIC) and dense granule (GRA) proteins were obtained from ToxoDB (Protocol: http; Domain: toxodb; Top level domain: org). The coding regions were analyzed for the presence of predicted transmembrane or signal peptides using the ExPASy server (Protocol: https; subdomain: www; second level domain: expasy; Top level domain: org). Proteins were expressed either as full-length proteins or as truncations that were designed to eliminate undesirable hydrophobic regions. Genes were cloned from cDNA produced by Superscript III (Thermo Fischer Scientific) reverse transcriptase priming from polyA mRNA isolated from the type II ME49 strain, according to the manufacturer's recommendations. Primers to the coding regions of interest were designed to contain a BsaI site at the 5 end, and a XbaI site at the 3 end, in order to be compatible with the N-terminal His-tagged SUMO system from LifeSensor (pE-SUMO vector). PCR amplicons containing the region of interest were digested with BsaI and XbaI and cloned into similarly prepared pE-SUMO vector and transformed into competent XL1-Blue *E. coli*. Ampicillin resistant transformants were checked by PCR amplification and Sanger sequencing to verify plasmid inserts. To express recombinant proteins, pE-SUMO vectors containing inserts of *T. gondii* genes were transformed into BL21(DE3) Rosetta pLysS *E. coli* cells grown in terrific broth (TB) or Luria broth (LB). For induction of protein expression, cells were grown as a 5 ml overnight culture, then diluted 1:1,000 in fresh LB or TB and cultured at 37° C. for 4-6 hr followed by addition of IPTG (0.5-1.0 mM) and culture at 15° C. overnight. Protein expression and solubility were tested by lysis of the cell pellet in CelLytic B buffer (Sigma-Aldrich) and separation of pellet and supernatant fractions that were analyzed by SDA PAGE.

Proteins were purified using His-select nickel affinity columns (Sigma-Aldrich), and eluted in 200-300 mM imidazole, 50 mM sodium phosphate pH 8.0, 300 mM NaCl, according to the manufacturer's instructions. In cases where the SUMO tag was removed, proteins were first bound to nickel beads and then treated with purified SUMO protease U1P1 that was cloned as a N-terminal fusion in pET22b (Novagen) and separately produced in *E. coli*. The His-tagged SUMO and His-tagged protease were bound to the His-select nickel beads and the eluted fraction was analyzed for enrichment of the cleaved recombinant *T. gondii* protein. Proteins were checked for purity and concentration by SDS PAGE stained with Coomassie Blue or Syrpo Ruby. Proteins were dialyzed against 150 mM NaCl, 50 mM Tris-HCl, pH 8.0 and stored in aliquots at a concentration of 0.3 μg/μl at −80° C. until used.

The purified recombinant proteins elicited strong responses in the Limulus amebocyte assay (LAL), the gold standard for monitoring lipopolysaccharide (LPS). To alleviate this problem, we treated the recombinant proteins with polymyxin B resin, an antibiotic that binds LPS (*Endotoxin removal from protein solutions*. Petsch D, Anspach F B. J Biotechnol. 2000 Jan. 21; 76(2-3):97-119). Recombinant proteins were incubated with Polymyxin B agarose-endotoxin removal resin (Sigma, USA) for 6-12 hrs at 4° C. using gentle end over end mixing to achieve an endotoxin level <0.1 EU/mg. Then, the proteins were eluted using endotoxin-free buffer containing Tris-HCl at pH 6-8 depending on the protein. The amount of residual LPS in the proteins preparation were checked using a LAL assay kit (Pierce, USA) according to the manufacturer's instructions. Purified endotoxin-free proteins were then filter sterilized, quantified and stored at −80° C.

Chronic Mouse Infections

Specific-pathogen-free mice were obtained from Jackson Laboratories and housed in the Animal Care Facilities at Washington University School of Medicine. Animals were housed and cared for according to the NIH Guide for the Care and Use of Laboratory Animals as approved by the Animal Studies Committee at Washington University.

Female C57/BL6 or Balb/C mice, age 8-12 weeks, were infected with the type II strains PRU or ME49 by i.p. needle inoculation of tachyzoites grown in vitro, using procedures described previously [4]. Alternatively, naïve animals were infected by oral feeding of 5-10 tissue cysts from chronically infected mice, as described previously [4]. To prevent accidental death during acute infection, mice infected with the ME49 strain were given sulfadiazine in the drinking water (0.1-0.2 g/L) 4-10 days post infection. Chronic infections were confirmed by serological analysis of serum obtained 30 days post infection, as described previously [4].

In Vitro Assays for IFN-γ Secretion

To obtain T lymphocytes for ELISpot analysis, we isolated splenocytes from naïve and $T.$ $gondii$ chronically infected mice. Spleens were harvested and splenocytes were isolated by passage through a 70-μm-pore-size nylon cell strainer. Splenocytes were pelleted and red blood cells (RBCs) were removed using RBC lysis buffer (Biolegend, USA) for 5 min at 4° C. Splenocytes were then washed in sterile PBS and HBSS media (Corning, USA). Splenocytes were finally resuspended in CTL-media (CTL, USA) supplemented with 1% L-glutamine and 1× Pen-strep antibiotics.

ELISpot assays were conducting in 96 well plate format using splenocytes isolated as described above. Briefly, 2.5× $10^5$ cells per well were plated in 96-well plate pre-coated with murine IFN-γ capture antibody (Immunospot, CTL, USA) and cultured for 24 hrs with media alone, purified recombinant proteins (2 μg/ml), a recall positive control-ESA (2 μg/ml), a T cell non-specific positive control Con A (2 μg/ml) and purified recombinant control protein-SUMO (2 μg/ml) at 37° C. with 5% $CO_2$. After washing and developing the plate according to the manufacturer's instructions, the antigen recall response was determined by counting the number of spots (IFN-γ producing cells) per well per treatment. The number of IFN-γ producing T-cells following stimulation with $T.$ $gondii$ antigens, were detected and calculated using an ELISpot reader (Immunospot®S6 Core, CTL, USA).

Antigen Injection and Monitoring of Luminol Reaction

Control or chronically $T.$ $gondii$ infected mice were used to test the delayed type hypersensitivity (DTH) response using a previously published protocol for monitoring luminol fluorescence after in vivo injection [5]. Control or chronically infected mice were injected with PBS, ESA proteins (1.5 ug/in 10 μL injection volume). Animals were injected s.c. either in the pinne of the ear (using PBS control on one side and antigen on the other) or s.c. in the back of the animal after it had been shaved to remove fur. At 24, 48, or 72 hr post injection, mice were anesthetized using isoflurane, injected i.p. with luminol (10 μL/gram of body weight of a 20 mg/ml stock) and imaged using an IVSI Spectrum in vivo Imaging System with exposure settings of 1-3 sec. Data were analyzed using the IVIS Living Image software to determine the relative light emission for the region where antigen was injected, compared to a neutral background region or to the PBS control injection. Data were graphed and analyzed using Prism (GraphPad).

MIC1 Predicted Protein Sequence Type II ME49:

(SEQ ID NO: 1)
MGQALFLTVLLPVLFGVGPEAYGEASHSHSPASGRYIQQMLDQRCQEIAA

ELCQGGLRKMCVPSSRIVARNAVGITHQNTLEWRCFDTASLLESNQENNG

VNCVDDCGHTIPCPGGVHRQNSNHATRHEILSKLVEEGVQRFCSPYQASA

NKYCNDKFPGTIARRSKGFGNNVEVAWRCYEKASLLYSVYAECASNCGTT

WYCPGGRRGTSTELDKRHYTEEEGIRQAIGSVDSPCSEVEVCLPKDENPP

VCLDESGQISRTGGGPPSQPPEMQQPADRSDERGGGKEQSPGGEAQPDHP

TKGGNIDLPEKSTSPEKTPKTEIHGDSTKATLEEGQQLTLTFISTKLDVA

VGSCHSLVANFLDGFLKFQTGSNSAFDVVEVEEPAGPAVLTIGLGHKGRL

AVVLDYTRLNAALGSAAYVV EDSGCSSSEEVSFQGVGSGATLVVTTLGE

SPTAVSA

The Form of MIC1 Used in the Assay (in Bold Above):

(SEQ ID NO: 2)
His-SUMO-(M)AYGEASHSHSPASGRYIQQMLDQRCQEIAAELCQGGLR

KMCVPSSRIVARNAVGITHQNTLEWRCFDTASLLESNQENNGVNCVDDCG

HTIPCPGGVHRQNSNHATRHEILSKLVEEGVQRFCSPYQASANKYCNDKF

PGTIARRSKGFGNNVEVAWRCYEKASLLYSVYAECASNCGTTWYCPGGRR

GTSTELDKRHYTEEEGIRQAIGSVDSPCSEVEVCLPKDENPPVCLDESGQ

ISRTGGGPPSQPPEMQQPADRSDERGGGKEQSPGGEAQPDHPTKGGNIDL

PEKSTSPEKTPKTEIHGDSTKATLEEGQQLTL

MIC1 Coding Sequence (Introns Spliced Out, Coding Region in Bold) Type II ME49:

(SEQ ID NO: 3)
acctgaaagcgggtgccgcgtcgctaccgtttcctgtggcgtctctagtg cgacatccgaagtaacagtaacgtccggcatggaacgccgacgcgggtgt tccagtcgcctggctccttctactcgcacttcgatgttacgttccttatt ggtgcgacgcggttctcgtgttgctagacgtcgcaccggctgaaagctgt agaaaatttagttattttcctgtcagctagcttgcaggagtgcgttttg tgtgttggtttcgtctcacatggctgctgatctgttgatgcagctgta cacgtgcctcgattctgtagttgacctagaacggatttgcaaagATGGGC

CAGGCGTTGTTTCTCACCGTTCTATTGCCGGTGTTATTTGGCGTTGGGCC

AGAAGCATATGGAGAAGCGTCGCATTCTCATTCGCCGGCATCGGGACGTT

ATATACAACAGATGCTTGACCAACGCTGCCAAGAGATTGCTGCAGAACTC

TGCCAAGGCGGACTTCGTAAAATGTGTGTGCCCTCTAGCCGGATAGTAGC

TCGAAACGCCGTGGGCATTACTCATCAAAATACACTTGAATGGAGATGCT

TTGATACAGCCTCTTTGCTGGAGAGCAATCAAGAAAACAACGGTGTTAAT

TGCGTGGACGACTGTGGCCACACGATACCGTGTCCTGGCGGCGTACACCG

GCAAAACAGTAATCACGCAACGCGCCATGAGATACTGTCCAAATTGGTCG

AAGAAGGAGTACAACGGTTCTGCAGTCCTTATCAAGCATCTGCCAACAAG

-continued

```
TACTGTAACGACAAATTTCCAGGGACCATTGCGAGGAGGTCGAAGGGCTT

CGGAAACAATGTCGAGGTTGCGTGGAGGTGTTACGAGAAGGCCAGCTTGC

TGTACTCGGTTTATGCTGAGTGTGCGAGCAACTGCGGAACAACGTGGTAC

TGCCCTGGAGGACGACGAGGGACGTCGACAGAACTAGACAAGCGGCATTA

TACAGAAGAGGAAGGAATTCGCCAGGCAATCGGATCCGTCGACAGCCCAT

GTTCTGAAGTTGAAGTCTGCCTACCGAAGGATGAGAATCCCCCGGTGTGT

TTAGATGAAAGTGGCCAGATTTCACGAACTGGTGGTGGGCCACCGTCACA

ACCGCCTGAGATGCAACAGCCCGCCGATCGTTCGGACGAGAGAGGTGGCG

GTAAGGAACAGTCGCCTGGAGGAGAAGCTCAGCCGGACCATCCAACGAAG

GGTGGTAACATAGACCTGCCTGAGAAATCAACATCTCCCGAGAAGACGCC

GAAAACCGAGATCCATGGTGACAGCACGAAAGCGACGCTCGAAGAGGGGC

AGCAACTAACGCTCACGTTTATCTCCACTAAACTGGATGTTGCTGTAGGC

TCGTGTCATTCACTCGTCGCGAATTTCCTTGATGGATTTTTGAAGTTTCA

GACGGGCTCAAATTCGGCGTTCGATGTGGTAGAAGTGGAAGAGCCAGCAG

GACCCGCAGTGCTTACGATAGGTCTGGGACACAAAGGCCGTCTCGCTGTT

GTCCTCGACTACACCAGGCTCAATGCTGCTTTAGGATCAGCTGCTTACGT

GGTCGAAGATTCTGGATGCAGCTCAAGTGAAGAGGTTAGTTTCCAAGGAG

TGGGTAGTGGAGCGACGCTCGTGGTGACGACGCTTGGCGAGAGTCCTACG

GCCGTCTCTGCTTGAtttatagtactctttggagcatgcttgtggaggaa cgggacaatctcggcaaaatcaggatgaagtttgtgagatacagatcgtt cctgaacagtggaagatgcgtcactattacacctatatgcgtcctggttc ttgtagagttggagttcttgcaggtgtaatgactatgacatacggatata acttcatacggggaactgtg
```

Primers Used for Cloning:

```
MIC1(20-340) Bsa1-F:
                                        (SEQ ID NO: 4)
ACTGTGGTCTCTAGGTATGGAAGCATATGGAGAAGCGTCGCATTCTCA

MIC2(20-340) XBA1-R:
                                        (SEQ ID NO: 5)
ACTGTTCTAGATCAGAGCGTTAGTTGCTGCCCCTCTTCGAGCGTCGCTT
```

MIC3 Predicted Protein Sequence Type II ME49:

```
                                       (SEQ ID NO: 50)
MRGGTSALLHALTFSGAVWMCTPAEALPIQKSVQLGSFDKVVPSREVVSE

SLAPSFAVTETHSSVQSPSKQETQLCAISSEGKPCRNRQLHTDNGYFIGA

SCPKSACCSKTMCGPGGCGEFCSSNWIFCSSSLIYHPDKSYGGDCSCEKQ

GHRCDKNAECVENLDAGGGVHCKCKDGFVGTGLTCSEDPCSKRGNAKCGP

NGTCIVVDSVSYTCTCGDGETLVNLPEGGQGCKRTGCHAFRENCSPGRCI

DDASHENGYTCECPTGYSREVTSKAEESCVEGVEVTLAEKCEKEFGISAS

SCKCDNGYSGSASATSHHGKGESGSEGSLSEKMNIVFKCPSGYHPRYHAH

TVTCEKIKHFALDGAGNHDTTTYVARRRYPASL
```

The Form of MIC3 Used in the Assay (in Bold Above):

```
                                       (SEQ ID NO: 51)
YHPDKSYGGDCSCEKQGHRCDKNAECVENLDAGGGVHCKCKDGFVGTGL

TCSEDPCSKRGNAKCGPNGTCIVVDSVSYTCTCGDGETLVNLPEGGQGC

KRTGCHAFRENCSPGRCIDDASHENGYTCECPTGYSREVTSKAEESCVE

GVEVTLAEKCEKEFGISASSCKCDNGYSGSASATSHHGKGESGSEGSLS

EKMNIVEKCPSGYHPRYHAHTVTCEKIKHFALDGAGNHDTTTYVARRRY

PASL
```

Coding Sequence (Introns Spliced Out, Coding Region Bold) Type II ME49:

```
                                       (SEQ ID NO: 52)
tcttctcttcttccgtacttttccctgcatttcacacccctggtatgac tccacaccgcgtgtaaatgtcccttaggtgacacccgcagcagcgcgta ggaggaagtagatgtcagtgtagacgttttttgagatgagagacgataac gtaaaatgccgccgataacttctgcattatacacactctctctccacgc ctaggatgacaggtacggcggcacacggaggaaagtggggggggggggg ggggcgaacagaaaggtcacatggaaggccgctcgactctccactcacg aagtgaaggcttcgtcccgttttgctggacaacgaatgcgaacttcttc actcgcttgtgacacacaactccagaggcacagagatgtgaagcaga agagtggcgtgtgcgtcgcttctgtcggcggcaagcccgctccgtctc tttggtggcgattctggtgtgcaccgtgtgccaagaagttgcgtgtcac gcgacttttggaaatgcatcaggttcagagtcgttatgttgcgattcag gctctcggcagagaatcatttccctgtaagctagttgaactcgccttt taaaagcggcagcagtgcccttgtggaaggcctcactgtgcctactttc ctcgtcctgagttttccgccttcggcctcatttttgctcaccaaaat cgtgtcctaccgtcaagttttgccatagactcctacgggaaaaaacaag ccggtcgacacggacgacgcccgcagggaagcgtcccctccgcagaaat cgggagacaactgtcgttgacggtgctgcgcgaaaggtcacagagtttc cagtgtgttcatcagacctcactgtgcactgttagcggccgctgtcccg cctggtcaacaagtatcacaccctcgtccccgccattggcacggagctc gatgagctgcagtgtcgcttttaggggagtcgtgcaatcacgccgcaac acaggcgtgattcgatcttcaattgctaggtaaccactcgtgcttggta gctctgcaatggctcgagcgacggggtgatgcaacatgctgctaaaaa ctcgacagacgtgtcaccggaacccacctaaataggagaccacgggtct ctggtgtgtcgcgtcgcattctcgcgtcgcattctcgcgtcgcaatgac cggccagttgctcgacgtcgccagccgggactgaagagcgttcatcgag tcagcagcattgcgtcccttgctcggtgaaaaaagactctctggtcga gtctagctcgtgtcacttctgtttctaacctccttcgttcaccggtaca cctccgatgtgacttttggtacacttgccctgtcgcacgacgcacgctg tcactcaacttgctgctagcgcaatcgataggttccctcgaaccagcca tcacacacacaccttttccgggaagacgtttgcgggcggtgggtcgcag
```

-continued
```
ctcgtcgagagtgcgttctgtgcatttctgtgggcagtgcagcgctt tgcgcgccttactctgtgtgtaacttccttgtccaacactggtaaaaAT

GCGAGGCGGGACGTCCGCGCTGTTGCACGCGCTCACCTTCAGTGGGGCC

GTGTGGATGTGCACCCCAGCGGAGGCTTTGCCGATTCAGAAGTCTGTGC

AGCTGGGCAGCTTTGACAAAGTTGTGCCGAGCCGCGAAGTCGTCTCTGA

GAGTCTTGCTCCGTCTTTCGCGGTGACTGAGACTCACTCGTCTGTGCAA

TCCCCCAGCAAGCAGGAGACGCAACTCTGTGCTATCTCGAGTGAAGGCA

AGCCATGTCGAAACCGTCAGTTGCACACTGACAACGGGTACTTCATCGG

GGCCAGTTGCCCCAAGAGCGCTTGCTGCAGCAAGACCATGTGCGGCCCC

GGCGGCTGCGGAGAATTCTGCTCCAGCAACTGGATTTTTTGCAGCAGTT

CGCTCATCTACCATCCTGACAAAAGCTATGGAGGAGACTGCAGCTGTGA

AAAGCAGGGCCATCGGTGCGACAAAAACGCAGAATGCGTCGAAAACTTG

GACGCGGGTGGGGGTGTGCACTGCAAGTGCAAAGACGGCTTCGTCGGCA

CTGGGTTGACTTGCTCCGAGGATCCTTGTTCAAAAAGAGGGAACGCGAA

GTGCGGACCCAACGGGACGTGCATCGTCGTCGATTCAGTCAGCTACACA

TGCACCTGCGGCGACGGCGAAACTCTAGTGAACCTCCCGGAAGGGGAC

AAGGATGCAAGAGGACTGGATGTCATGCCTTCAGGGAGAACTGCAGCCC

TGGTAGATGTATTGATGACGCCTCGCATGAGAATGGCTACACCTGCGAG

TGCCCCACAGGGTACTCACGTGAGGTGACTTCCAAGGCGGAGGAGTCGT

GTGTGGAAGGAGTCGAAGTCACGCTGGCTGAGAAATGCGAGAAGGAATT

CGGCATCAGCGCGTCATCCTGCAAATGCGATAACGGATACTCCGGATCT

GCTTCCGCAACCTCCCACCATGGGAAAGGAGAATCGGGATCCGAGGGGA

GCTTGAGTGAAAAAATGAATATTGTCTTCAAGTGCCCCAGTGGCTACCA

TCCAAGATACCATGCCCACACCGTGACGTGTGAGAAAATTAAGCACTTT

GCCCTTGACGGGGCCGGCAACCACGACACGACTACGTATGTCGCAAGAC

GAAGGTACCCAGCGAGTCTCTGAgagcggagatcagcgcaaagacaaga tgcagagtttgactcgagaaacaatagtaacacgaagtaaaaagtctcc acactaagccaaggattgagaatatttcgatttgtgccgctggcaatag tggccttggcctagaaagaagttctgcaacgaagcgatcggctcacacg cggatacacagatgggtttgtaccgagaacgttaggtttgtgaaccgag ttcaggtaaaacaaagtagattgtgcctttacgcagacagcgagggaaa acatgaggacacactgccaactaaagcaagactgcctcactaattacca ccgacacacgacatggttaccccgcgttttgccgcgtgcaaagtttga attctgatggttctcgagtctgaaagcctaaaccgcccaaccatgtatg aaataagaacccatcaaacgtgagacatctctgccgaagtgcctacgaa aagaacgcttctgccactaggaggtgcggcctcttcattctatgagaac ctgctttgtcggtgtcaacctctggggaaatcgcctgcctttacacatt ttgctcgttgtagagcaagggatctgttgctgcgtttactccaatacaa tgatcgccgtttcgctgtaggcaagcgatccgaaaatgtacgttcgagt cagcagctacttgagaagcagccaacgccgacacttgctgcgtttgact gaggtgcactcgcaaacagtctcgtctccccggggcaatttctgagaga
```
-continued
```
aatgcgggaatggacgtaatggtgctcttctgtgagtgctcttccacca attttttcgacaagtgttttcgtgacagtcgagtataccttcttatgtca ttctgtctccgtcagtgctatcggattcttcctattcctctacccttc tacagtcgcatacaaagctgctgaaacaagacttcctttgtctagggta gttgtacactccacacatatctgactgaaacctacggcaggaagtctgg tcggcactgtgcttccttgttggcttttcgtcgtttctttgtctacgag cttcactgggtccttgacacggcttgtgagcgttgtgctcaatattcga ccagctgtatttgtg
```

Primers Used for Cloning:

MIC3F (134-383)-BsaI-F
(SEQ ID NO: 53)
ACTGTGGTCTCTAGGTATGATCTACCATCCTGACAAAAGCTATGGAGGAG
ACT

MIC3F (64-383)-BsaI-R
(SEQ ID NO: 54)
ACTTGTTCTAGATCAGAGACTCGCTGGGTACCTTCGTCT

MIC4 Predicted Protein Sequence Type II ME49:

(SEQ ID NO: 55)
MRASLPVHLVVCTQLSAVWFGVAKAHGGHRLEPHVPGFLQGFTDITPAG

DDVSANVTSSEPAKLDLSCVHSDNKGSRAPTIGEPVPDVSLEQCAAQCK

AVDGCTHFTYNDDSKMCHVKEGKPDLYDLTGGKTASRSCDRSCFEQHVS

YEGAPDVMTAMVTSQSADCQAACAADPSCEIFTYNEHDQKCTFKGRGFS

AFKERGVLGVTSGPKQFCDEGGKLTQEEMEDQISGCIQLSDVGSMTADL

EEPMEADSVGACMERCRCDGRCTHETENDNTRMCYLKGDKMQLYSSPGD

RTGPKSCDSSCFSNGVSYVDDPATDVETVFEISHPIYCQVICAANPLCT

VFQWYASEAKCVVKRKGFYKHRKTGVTGVTVGPREFCDEGGSIRDREEA

DAVGSDDGLNAEATMANSPDFHDEVECVHTGNIGSKAQTIGEVKRASSL

SECRARCQAEKECSHYTYNVKSGLCYPKRGKPQFYKYLGDMTGSRTCDT

SCLRRGVDYSQGPEVGKPWYSTLPTDCQVACDAEDACLVFTWDSATSRC

YLIGSGESAHRRNDVDGVVSGPYTECDNGENLQVLEAKDTE

The Form of MIC4 Used in the Assay (in Bold Above):

(SEQ ID NO: 56)
SEPAKLDLSCVHSDNKGSRAPTIGEPVPDVSLEQCAAQCKAVDGCTHET

YNDDSKMCHVKEGKPDLYDLTGGKTASRSCDRSCFEQHVSYEGAPDVMT

AMVTSQSADCQAACAADPSCEIFTYNEHDQKCTFKGRGESAFKERGVLG

VTSGPKQFCDEGGKLTQEEMEDQISG

Coding Sequence (Introns Spliced Out, Coding Region Bold) Type II ME49:

(SEQ ID NO: 57)
ttttctgtgcatctgtgctgcaaaacgggcctctgtgcattatttcccc accaacaattgccgcgtcgatccgggtcccgctcaagctctgcagaact -continued aggctctcgatatagatcagtacaatcattcgcttctgacaatcgcatc gactgagcgacgcgttgatcgtcgactgtcgtgcgtcgcattcgggcat ctcgaaccggtgttgattccctgtgtcattatttcacttccgtccttct ctcgtggcgatctataatacgcgtgtgttgttgcgtgcattgcttgtgt tgttgtggatgtgttttcttttgtgaccgctcacgaacaccccacgcaa aATGAGAGCGTCGCTCCCGGTTCACCTCGTTGTGTGCACGCAGCTAAGT

GCCGTTTGGTTTGGAGTGGCTAAAGCCCATGGTGGACACCGACTGGAAC

CGCATGTTCCCGGATTCCTGCAAGGCTTCACTGATATCACGCCTGCAGG

TGATGACGTTAGTGCCAACGTAACAAGTTCGGAGCCTGCAAAACTTGAT

CTCTCTTGTGTGCACTCTGACAATAAGGGATCAAGGGCTCCCACAATAG

GCGAGCCAGTGCCAGATGTGTCCCTGGAACAATGTGCTGCGCAATGCAA

GGCTGTTGATGGCTGCACACATTTCACTTATAATGACGATTCGAAGATG

TGCCATGTGAAGGAGGGAAAACCCGATTTATACGATCTCACAGGAGGCA

AAACAGCATCGCGCAGTTGCGATAGATCATGCTTCGAACAACACGTATC

GTATGAGGGAGCTCCTGACGTGATGACAGCGATGGTCACGAGCCAGTCA

GCGGACTGTCAGGCTGCGTGTGCGGCTGACCCGAGCTGCGAGATCTTCA

CTTATAACGAACACGACCAGAAATGTACTTTCAAAGGAAGGGGTTTTC

TGCGTTTAAGGAACGAGGGGTGTTGGGTGTGACTTCCGGGCCGAAACAG

TTCTGCGATGAAGGCGGTAAATTAACTCAAGAGGAGATGAAGATCAGA

TCAGTGGCTGCATTCAATTGAGTGACGTTGGATCAATGACTGCTGACCT

GGAGGAGCCTATGGAGGCTGATTCTGTTGGCGCTTGTATGGAACGGTGC

CGCTGTGATGGAAGATGCACGCACTTCACGTTAACGATAATACTCGGA

TGTGCTACCTCAAAGGTGACAAGATGCAGTTGTACTCATCTCCAGGTGA

CAGAACCGGCCCAAAGAGCTGCGATTCAAGCTGCTTCTCGAACGGGGTT

TCTTACGTCGATGATCCGGCGACAGATGTTGAGACCGTATTCGAAATTT

CACACCCAATTTATTGTCAAGTAATCTGCGCCGCAAATCCGTTGTGTAC

AGTGTTTCAGTGGTATGCCTCCGAGGCAAAGTGCGTCGTCAAGAGAAAG

GGGTTTTACAAACACAGAAAAACAGGTGTCACGGGAGTCACAGTGGGCC

CTCGGGAGTTCTGCGATTTTGGCGGTAGCATCCGCGACCGAGAAGAGGC

AGACGCCGTTGGATCAGACGATGGCCTCAACGCGGAAGCAACTATGGCA

AATTCTCCTGATTTTCACGACGAAGTAGAATGCGTCCACACGGGCAACA

TTGGGTCAAAAGCACAAACCATTGGAGAAGTGAAACGCGCAAGTAGTTT

GAGTGAGTGCAGAGCCAGATGCCAAGCGGAGAAAGAATGCAGCCACTAC

ACTTACAATGTAAAATCCGGTTTGTGTTATCCAAAAGAGGAAAGCCTC

AATTTTATAAGTATCTTGGCGACATGACGGGATCCAGAACATGTGATAC

AAGTTGCCTTAGGAGGGGAGTCGATTACTCACAGGGCCCTGAAGTAGGA

AAGCCTTGGTATTCTACGCTGCCGACAGACTGCCAAGTTGCATGCGACG

CTGAGGATGCTTGCCTGGTGTTCACCTGGGATTCGGCGACGTCACGATG

CTACCTCATCGGCTCAGGTTTCTCGGCACATCGACGAACGACGTGGAT

GGCGTGGTATCTGGACCCTATACTTTCTGTGACAATGGCGAAAACCTTC

AGGTGCTTGAAGCGAAAGACACAGAATGAcccaggagggtgccagatac

-continued tttgtgtgactgcgacatgcagtcatgtactcaaagtgttgtacatgga caggaggacttttttttaagtcattgcagaggtgcgttttcggagcag cactataactgcgtcagcgactaagcacgccacgtagctgaatgaaacg cagccaccttcgtgtatgtatgcttcgttttttgtcgctgtgcagtttt gaatcatttcccttatgggacatttctgaaaaatgctccccgttcgctt gtagcactatgagaggggccgaagactgcaatggaggtagcgctgcgtt gaaaagacgaggcgctacatttcgcgtagcgacaaggccgtgtagagtt ttgcttttcgcgagacactgctctgagtgtcatatgcatcaaatgcagt ggtagcacacagaggtgagaagaatgatcacctgcggggggaatggcttt gctaaacaacaaggtcgctgtgtgactttacacaacgaaactactgtgg tgagtgctcagttgagtgaaaagaaatgccgcgttatcgtgagttctgg ttcggtggactttgccaccgtagtaaaactcaacctgtaacggaatgcc cagttttactgctctcttttaaagggcgtccacgttctctatattcaagc tgtttaccacctgcgtttcggtgcatcgcgcgtgccacatcaaaaatc caggtaacggtgcgggacctatgctacactttatatctctcagaaagca tacacccactgattatggacaacgctgtggtcgcgttgtaccacaatgc aggaatactcagttcaccttgcaagtgttctggtgttcattgcgtgtca gaagtacacgaaaagagacttctttggcctccaagtgatacgtaaccgc ggcagtcatgaacagagtcactcgtgcttctgaaacgcacgtcttctgt acagagacagatgcagtgtgcatacaggaagcccctcgattgttgccgt agcaggtagccagtagaagaaacaaagacacggt Primers Used for Cloning:

MIC4 (58-231) -BasI-F
(SEQ ID NO: 58)
ACTGTGGTCTCTAGGTATGAGTTCGGAGCCTGCAAAACTTGATCTCTCTT

GTGT

MIC4 (58-231) -XBAI-R
(SEQ ID NO: 59)
ACTGTTCTAGATCAGCCACTGATATGATCTTCCATCTCCTCTTGAGT

MIC6 Predicted Protein Sequence Type II ME49:

(SEQ ID NO: 60)
MRLFRCCAAAVVAAESLLWLKNGSPFFAFLPGNGEIADNCSGNPCGGTAA

GTCINTPSGYDCRCEPGYVLGVENDQVTCMMPSGVPMANFVQLSEKPAAC

SSNPCGPEAAGTCNETNSGYICRCNQGYRISLDGTGNVTCIVRQESGCEE

NGCGPPDAVQSCRRLTGTAGRLCVCKENFIATIDASAHITCKRVPPHYRK

PPFEFGKGGHPVDSEPSKRQREDEGESREPESDSTEPGRDQERRTPLEES

QEPEGSTPDSQQSRGGSGSDSTESEEQGKEREEGSGHAGAIAGGVIGGLL

LLSAAGAGVAYMRKSGSGGGEEIEYERGIEAAEASEVEVLVDLDSKTWD

The Form of MIC6 Used in the Assay (in Bold Above):

His-SUMO (SEQ ID NO: 61)
SPFFAFLPGNGEIADNCSGNPCGGTAAGTCINTPSGYDCRCEPGYVLGVE
NDQVTCMMPSGVPMANFVQLSEKPAACSSNPCGPEAAGTCNETNSGYICR
CNQGYRISLDGTGNVTCIVRQESGCEENGCGPPDAVQSCRRLTGTAGRLC
VCKENFIATIDASAHITCKRVPPHYRKPPFEFGKGGHPVDSEPSKRQRED
EGESREPESDSTEPGRDQERRTPLEESQEPEGSTPDSQQSRGGSGSDSTE
SEEQGKEREEGSGHAGAIAGGVIGGLLLLSAAGAGVAYMRKSGSGGGEEI
EYERGIEAAEASEVEVLVDLDSKTWD

Coding Sequence (Introns Spliced Out, Coding Region Bold) Type II ME49:

(SEQ ID NO: 62)
cagtccggagcacactcctacaataaacttgatacgtgtcattttgtgaa
acgacacagcacataaccactcggactgtctcacgaagctgtagggcgga
ttcaccaatgatctttcgcagccgatccaaaactacttgcccacttccgg
tgtacgtacatcgcgcgacatgagaggcattcattgttttccatagaaaa
cactactggacaaccattcggtagcgcacaagttgagcctctgacaaatc
tttcctcatcacgtgaatacacgctgcgtgattcgtcagtgactccactg
tggtcttttaaccaccatcagagtcctgtaagcatcctttgtttccgttta
aaatgcctgccagatggcacgacgccgtctggttttgccggctttctccg
agtcctattagactttgatgccttacggcttttttttaagaatggttctt
ttgagatttgccgactttccagttccgccaccagacgctcctgttgaact
gccaccggcacgatgcagtattccgccacgaaaacgcgcaccgcaagctc
cgctaccattaaacgggtttcgtctgctttagatgtttccttccgcgtca
tcaaggcaaaagcattgccactgatgttaccgaagctttcccgccatgct
gcgcacaatgcccaatcttccgtcacggacctcttccggtaaccacctaa
aggaggattactgggcaacccaaaacgctgcaacaagaagcacagtccag
gtgtcgctagattcgagcctgcatggtcgttccgtagctccatacaacaa
ttctctgtgtgacggcgagaggagtaacgcgctagtgtgtgtcagcgacg
cggcagtcgatccgatcctgcaacaggcagaggtgtgtcgatgctcagtg
atgcgacggcgtatctgaagaggactgtagctccaccacgaccttcgtgg
gagcacgaagtgtactctgttgtcgtcggtctcgtatttttttgagttgt
gtacttcgctgcaagaggagggtgagattcgacatctgtgggcgtttggg
atcgtgatgacatcgactgtgctttgatatatgatgtgttttttttcgat
tggatgagcacattccagtaagcttcctgccgcgcgtctctgct**ATGAGG
CTCTTCCGGTGCTGTGCTGCGGCCGTTGTGGCGGCCGAATCGTTACTGTG
GCTGAAGAACGGCTCCCCGTTTTTTGCCTTTCTTCCTGGGAATGGAGAGA
TTGCAGACAACTGCTCTGGGAATCCATGCGGTGGCACCGCAGCTGGTACG
TGCATAAACACACCATCTGGATATGATTGCAGGTGCGAACCAGGCTACGT
TCTGGGCGTTGAAAATGACCAGGTCACGTGCATGATGCCCTCAGGTGTAC
CCATGGCTAATTTTGTACAGCTGTCGGAAAAGCCTGCAGCTTGCAGCTCA**

AACCCTTGTGGACCTGAGGCAGCCGGCACCTGCAACGAGACAAACAGTGG
TTACATTTGCCGCTGTAATCAAGGCTACAGAATATCTCTCGACGGGACAG
GAAACGTGACATGTATTGTAAGACAGGAAAGCGGCTGTGAGGAAAACGGG
TGTGGGCCGCCAGATGCAGTACAGAGTTGCCGCCGACTAACAGGGACGGC
AGGTCGACTATGTGTATGCAAGGAAAACTTTATAGCGACAATCGACGCCA
GTGCCCATATCACCTGCAAGCGTGTGCCTCCCCATTATAGGAAGCCTCCC
TTCGAATTTGGCAAGGGAGGTCATCCTGTGGACTCAGAACCATCGAAACG
CCAGAGGGAAGATGAAGGTGAAAGTCGTGAGCCTGAAAGCGACTCAACAG
AACCGGGGAGAGATCAGGAAAGAAGAACACCACTTGAGGAAAGCCAGGAA
CCGGAAGGAAGCACCCCGGACAGTCAGCAGAGCCGAGGTGGTTCTGGTAG
CGACAGTACCGAGAGCGAGGAACAAGGAAAGGAGAGAGAGGAAGGAAGTG
GACATGCTGGTGCGATCGCTGGGGGAGTTATTGGAGGCCTGTTACTTCTG
AGCGCTGCCGGAGCGGGTGTTGCATACATGAGAAAGAGTGGGAGCGGTGG
AGGGGAGGAGATAGAATACGAGAGGGGTATCGAGGCTGCAGAGGCCAGTG
AAGTCGAAGTCCTCGTTGATTTGGATAGCAAAACATGGGATTAAcacgtt
ctcggctgagacttcacaatgtagggtgtcgctggcagatcagctgcaat
gcgagaggtgacgcgagtagtgagcaccgcttcttttaagcgcggacatt
gtgctcggtcttctgtcaccccgaatcaaaacacatgtatgataatagt
tcctgttgacttccctgccgacaaagaactgctgtgtcgaggccggctt
ctgtgcactcatcccaaatgagatggactgatgttttagagacacctcat
cgccgacggaaaccatcagctcccagagaaactatgctgcgtcgttttt
aggtgatctgttgcgtaatgcgcaccttcatatcatctgtgtgttgactg
tttggtcgttttccgtttagtcaaatgaatgcagtgaaatgcagggaatt
tagcagacaccgagaactgtcctcttgttctgtgcgcgagttgttttttaa
cgtatagcgatgcgtttgcacttgatattaccctaagccatcagtgggta
tttagaggagcccacaggtgatgggggtgatccctgtttcttgtcatttg
gcttgtagggttcgctggaactatctggtgtcacggaagagtggcttttac
tgtctgtccccaaacgcaaggcatcagtgtaaccccgataggactctgga
gacttctgcttcactgccgcgttgcaattttcccgcgtcatgtggcaata
acggtaattccacgtgcacgccgcataccggatctttgctcccaggcttt
cttatgaggtcggcatacgtacagcggcggcgtacctccgctctagaa
gaccggtccaaccgactttgaacagcatgcttgtgaatgagtgcttaaac
accctgaagtgatggtggaatgtagcagtctgggacggttgatgcgagga
tatcaccattagcatagactaccttgctctttagcgaggcgagacaactt
atttaggtagccatgaaacacctcgatagtatcaatgacgacgtgcggtt
caccaacttccgtcgctagcgcagaaaacagtcggaaacacaactcggtg
agcacctgaagtgtcagtacacattcgaccgtcgggaccgggattccgc
aagtggcacccgctggtccagtagcaggaacctagttcattcagtataac
agatttgggcggcaaagagcaatttgctcgacctaacgcttgc Primers Used for Cloning:

MIC6-(24-349)-BasI-F
(SEQ ID NO: 63)
ACTGTGTGCTCTAGGTATGTCCCCGTTTTTTGCCTTTCTTCCTG

MIC6-(24-349)BasI-R
(SEQ ID NO: 64)
ACTGTTCTAGATTAATCCCATGTTTTGCTATCCAAATCA

SUMO Protein Sequence:

This sequence is present at the N-terminus of SUMO fusions

Coding Sequence for His Tagged SUMO (his-SUMO)

(SEQ ID NO: 16)
ATGGGTCATCACCATCATCATCACGGGTCCCTGCAGGACTCAGAAGTCAA

TCAAGAAGCTAAGCCAGAGGTCAAGCCAGAAGTCAAGCCTGAGACTCACA

TCAATTTAAAGGTGTCCGATGGATCTTCAGAGATCTTCTTCAAGATCAAA

AAGACCACTCCTTTAAGAAGGCTGATGGAAGCGTTCGCTAAAAGACAGGG

TAAGGAAATGGACTCCTTAAGATTCTTGTACGACGGTATTAGAATTCAAG

CTGATCAGGCCCCTGAAGATTTGGACATGGAGGATAACGATATTATTGAG

GCTCACCGCGAACAGATTGGAGGT

Predicted Protein Sequence for his-SUMO:

(SEQ ID NO: 17)
MGHHHHHHGSLQDSEVNQEAKPEVKPEVKPETHINLKVSDGSSEIFFKIK

KTTPLRRLMEAFAKRQGKEMDSLRFLYDGIRIQADQAPEDLDMEDNDIIE

AHREQIGG

Example 2

We have developed an efficient assay where we can control the amplitude of antigen release pharmacologically. We compared constitutive secretion (mock treatment), to conditions where we block or enhance microneme secretion. *T. gondii* antigens released into the extracellular milieu are likely to stimulate both humoral and cell-mediated immunity. Identification of immunogenic proteins in ESA has led to improved diagnostic reagents for *T. gondii* infection.

Collection of Excreted/Secreted Antigen (ESA)

*Toxoplasma gondii* RH strain parasites were isolated from infected human fibroblasts, filtered, and washed extensively. Parasites were either left untreated (Mock), treated to block (Inhibited), or induce secretion of ES antigens (Stimulated). After 10 min at 37° C., the parasites were chilled to 4° C., centrifuged, and the cell-free supernatant was collected. To evaluate the complexity, samples were separated by SDS-PAGE and the protein composition was assessed by staining. In addition, we used a luciferase-based assay to detect a microneme reporter to specifically determine the level of microneme secretion in each of the fractions (FIG. 1).

LC/MS-MS of ES Antigens

Samples were processed for mass spectrometry (MS), separated by LC, resolved on an Orbitrap MS/MS instrument, and analyzed using Mascot (Matrix Science, London, UK). Scaffold (Proteome Software Inc., Portland, OR) was used to analyze MS/MS peptides and establish protein identifications by comparison to gene databases.

We classified ES antigens based on enrichment of peptides in stimulated vs. blocked samples using a cutoff of 4-fold increase in two replicate samples. The proteins were further analyzed for their profile of expression during development to classify those that were bone fide micronemal proteins (the major component of ESA) vs. potential contaminants. The profile of micronemal proteins is highly characteristic and many of the secreted proteins share this transcriptional profile. Based on the fold enrichment and expression pattern, we generated a list of the most abundantly induced proteins in ESA (Table 1).

TABLE 1

Summary of ESA proteins identified by mass spectrometry.

| Gene ID | Product Description | Fold Increase[1] |
|---|---|---|
| TGME49_267680 | microneme protein MIC12 (MIC12) | 39.0 |
| TGME49_291890 | microneme protein MIC1 (MIC1) | 34.7 |
| TGME49_294330 | EGF family domain-containing protein | 34.0 |
| TGME49_208030 | microneme protein MIC4 (MIC4) | 28.8 |
| TGME49_201780 | microneme protein MIC2 (MIC2) | 27.3 |
| TGME49_319560 | microneme protein MIC3 (MIC3) | 26.1 |
| TGME49_206510 | toxolysin TLN4 (TLN4) | 25.0 |
| TGME49_214940 | MIC2-associated protein M2AP | 21.5 |
| TGME49_234380 | hypothetical protein (TGME49_234380) | 16.5 |
| TGME49_204050 | subtilisin SUB1 (SUB1) | 16.5 |
| TGME49_218520 | microneme protein MIC6 (MIC6) | 15.5 |
| TGME49_250710 | microneme protein MIC10 (MIC10) | 13.2 |
| TGME49_293440 | hypothetical protein (TGME49_293440) | 13.0 |
| TGME49_232280 | hypothetical protein (TGME49_232280) | 11.5 |
| TGME49_204130 | perforin-like protein PLP1 (PLP1) | 11.5 |
| TGME49_243930 | hypothetical protein (TGME49_243930) | 5.5 |
| TGME49_277080 | microneme protein MIC5 (MIC5) | 5.4 |
| TGME49_258870 | hypothetical protein (TGME49_258870) | 4.5 |

[1]Increase of peptide spectral counts in stimulated fraction vs. control

Example 3

Figure 2:
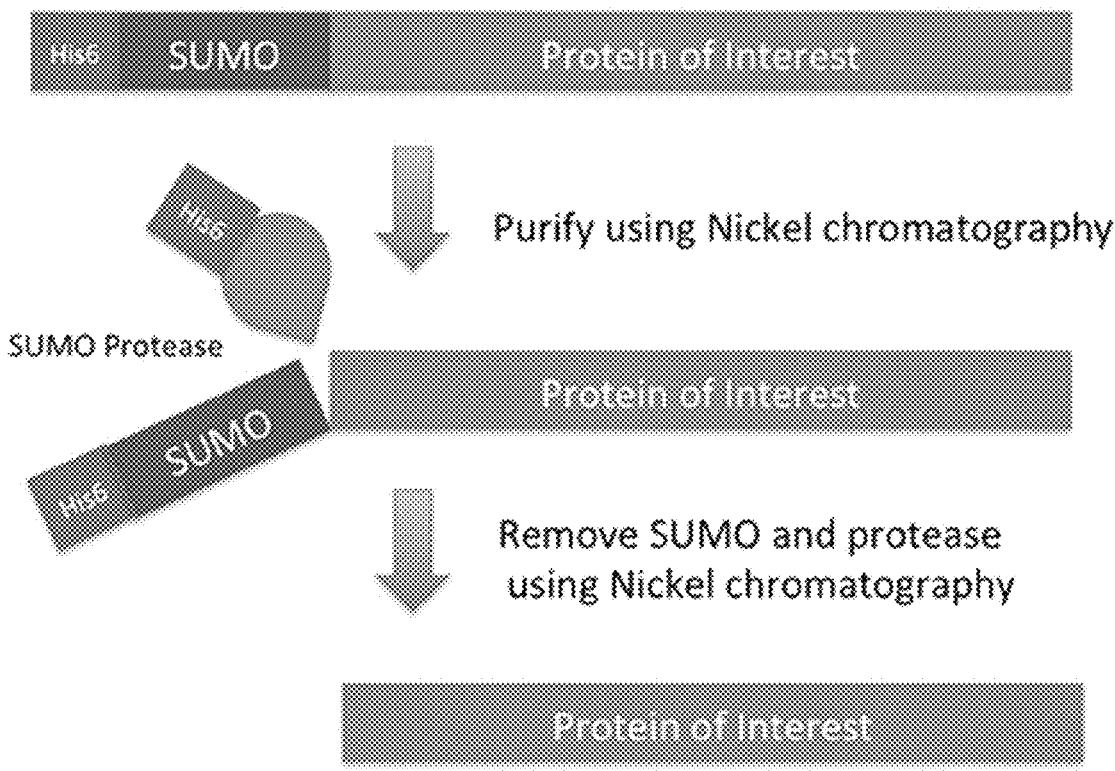
FIG. 2 shows an expression system for purification of fusion proteins. SUMO is a ubiquitin-like protein that is highly soluble, aiding in the expression of proteins in *E. coli*. Proteins can be cleaved by SUMO protease to release tag-free proteins of high purity. The SUMO-fusion protein and the SUMO protease are both tagged with six histidine residues that mediate binding to nickel, allowing one step purification by affinity chromatography.

To express these proteins recombinantly, we are using a fusion system based on the *E. coli* protein SUMO, which allows for production and purification of soluble, tagged proteins. From this group of initial candidates, we have successfully cloned, expressed, and purified all of the proteins shown in Table 2. These proteins were tested here as fusion proteins with SUMO as a control. However, they can also be purified away form SUMO after protease cleavage by nickel chromatography as shown in FIG. 2.

Example 4

Development of Model for DTH Using Bioluminescence

We tested an alternative method that relies on light production in the skin. The basis for this method is that recruitment of monocytes and neutrophils to the site of inflammation can be detected using luminol, a substrate that gives off light when converted by myeloperoxidase (Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461). This method has been shown to be sensitive for detecting DTH responses in the mouse and for monitoring leukocyte influx to sites of infiltration (Gross, supra).

Example 5

The Luminol DTH Response is Specific to ESA

Figure 3A:
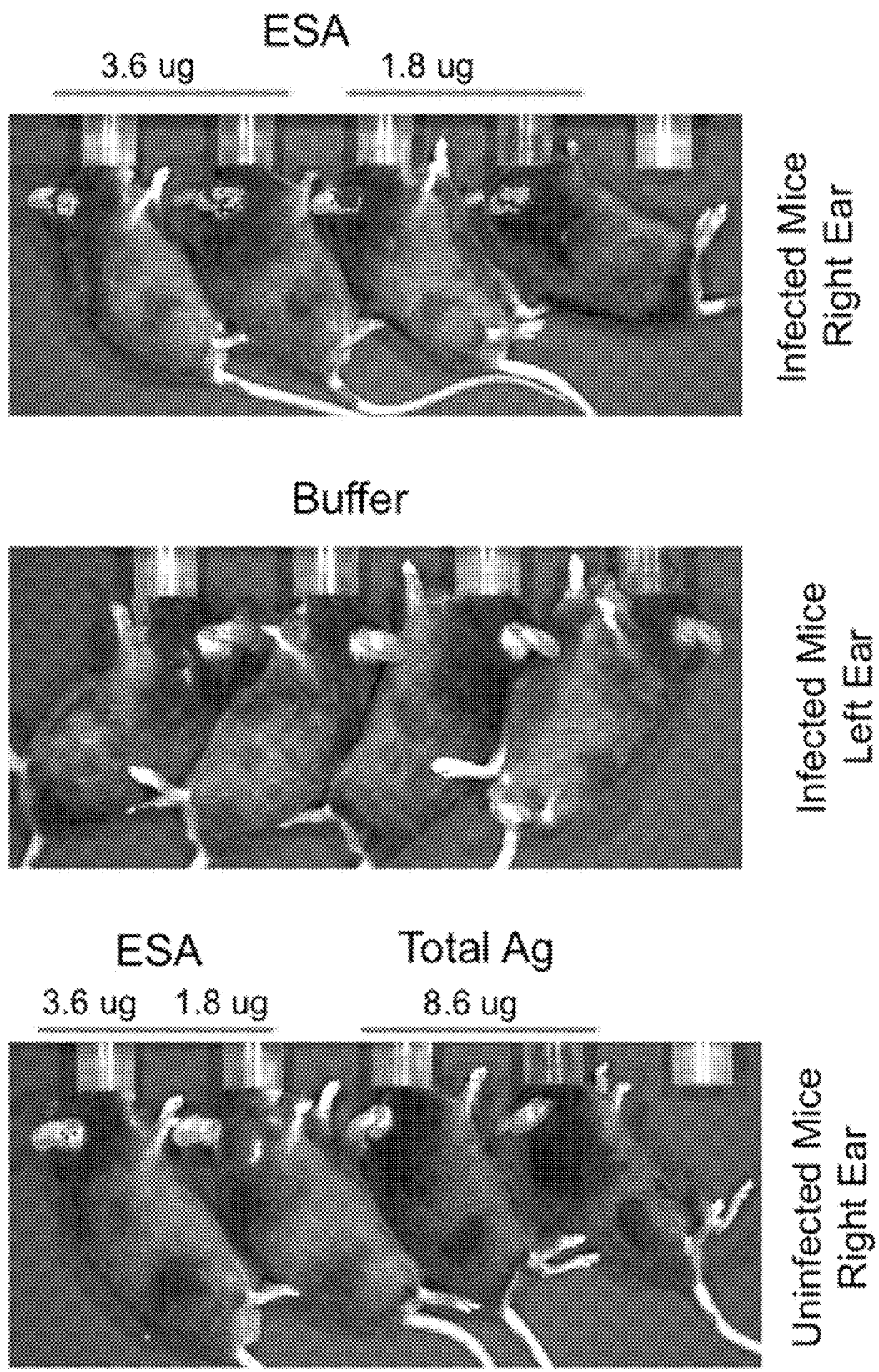
FIG. 3A-B shows luminol responses in mice.
Figure 3B:
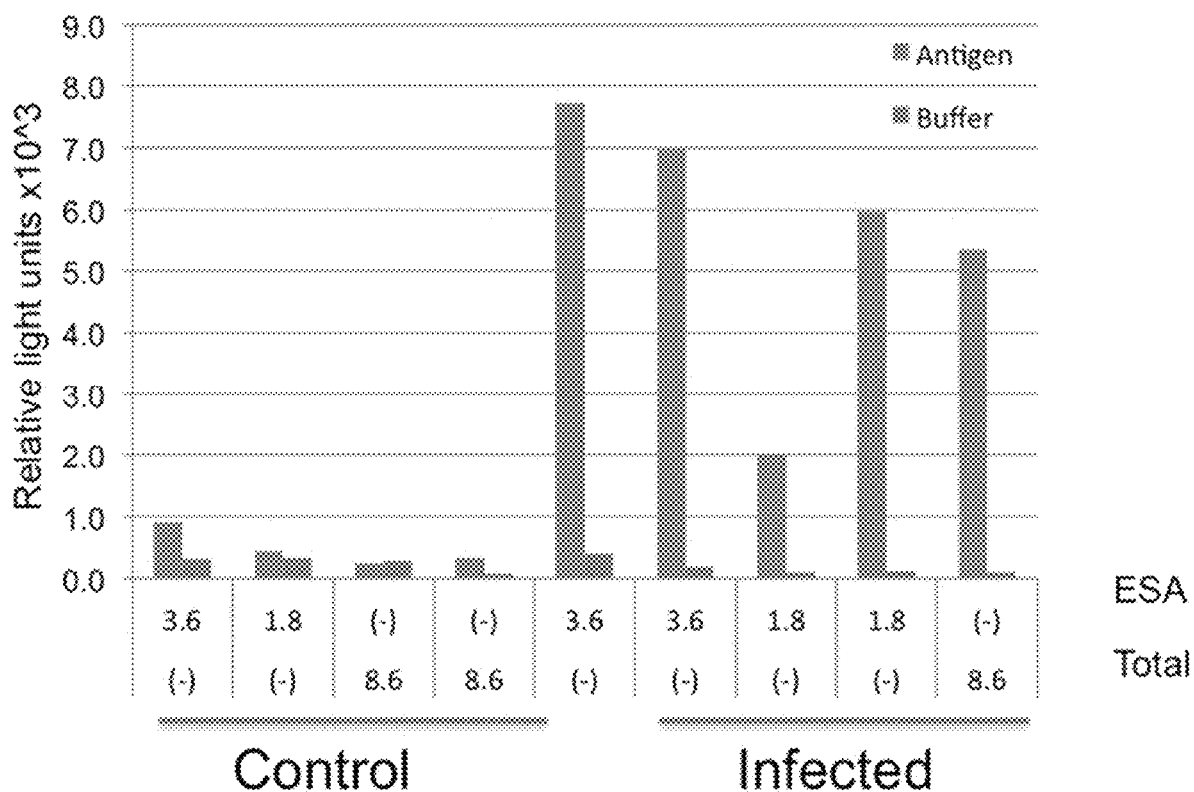

We have modified the luminol assay used for monitoring DTH responses in the mouse by injecting antigen in the pinne of the ear. In order to confirm that the DTH responses that we were detecting were in fact due to antigens in ESA, we compared the response for ESA to total parasite antigen or to PBS. The response detected by luminol was highly enriched in ESA sample compared to the PBS control or to total antigen (FIG. 3A, 3B). The response is also only seen in infected animals, confirming that it is due to a specific immune response. This experiment demonstrates that the DTH response is driven by antigens that are enriched in ESA.

Example 6

Figures 4, 5:
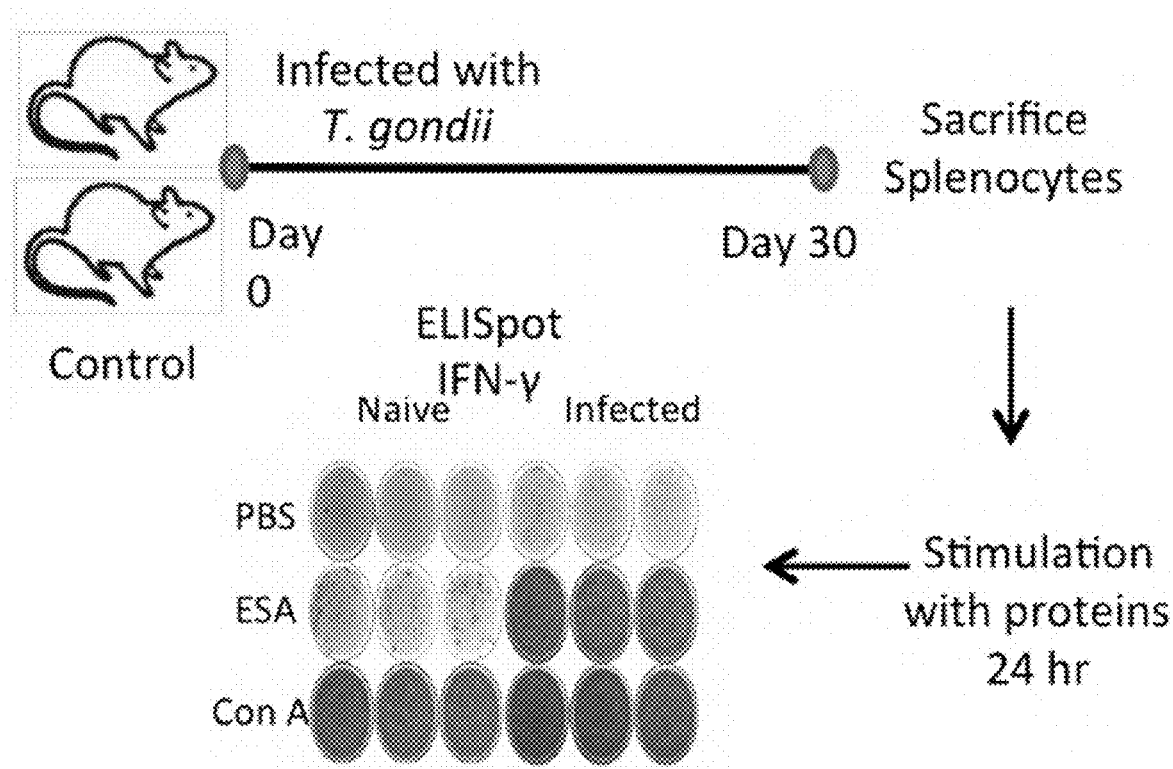
FIG. 4 Monitoring of lipopolysaccharide (LPS) using the limulus amebocyte assay (LAL). After purification over polymixin B resin, the level of LPS as monitored by the LAL assay was reduced by >50 fold.
FIG. 5 shows ELISpot assay detecting IFN-γ produced by splenocytes from naive and *T. gondii* infected mice. Samples treated with PBS or ESA during in vitro culture. Con A serves as a non-specific positive control.

We have focused on the ESA antigens defined in Table 1 along with some constitutively secreted dense granule proteins (GRA) that have previously been shown to be immunogenic. We have cloned, expressed, and purified 12 proteins for testing, as shown in Table 2. Test proteins were purified as fusion proteins with SUMO, an *E. coli* protein that facilitates solubility. We have also purified the SUMO protein as a control. To avoid non-specific responses due to endotoxin (LPS) we purified ESA proteins using polymyxin B, a detergent like molecule that removes endotoxin. The resulting purified proteins showed reduced levels of LPS when examined using the limulus amebocyte assay (FIG. 4).

TABLE 2

| ESA Protein | Constructs (aa) | Clone Vector | Strain | Molecular weight (kD) |
|---|---|---|---|---|
| MIC10 | Full length | pE-SUMO | Rosetta (DE3) | 23.1 |
| GRA7 | Full length | pE-SUMO | Rosetta (DE3) | 26 |
| GRA6 | Full length | pE-SUMO | Rosetta [DE3] | 25 |
| M2AP | Full length | pE-SUMO | Rosetta (DE3) | 34.6 |
| MIC5 | Full length | pE-SUMO | Rosetta [DE3] | 19.9 |
| MIC6 | Full length | pE-SUMO | Rosetta (DE3) | 36.7 |
| Hypothetic Protein 2 (TGME49_232280) | Full length | pE-SUMO | Rosetta (DE3) | 30.2 |
| GRA4 | 21-247 | pE-SUMO | Rosetta (DE3) | 38 |
| MIC1 | 20-340 | pE-SUMO | Rosetta (DE3) | 48.6 |
| MIC3 | 134-383 | pE-SUMO | Rosetta (DE3) | 40.5 |
| MIC4 | 58-231 | pE-SUMO | Rosetta [DE3] | 63.0 |
| Hypothetic Protein 1 (TGME.234380) | 89-347 | pE-SUMO | Rosetta (DE3) | 38.7 |

Example 7

An in vitro method to monitor antigen presentation This method is based on the ability of specialized immune cells (dendritic cells and macrophages) to present antigen to memory T-cells that in turn produce interferon gamma (IFN-γ). T-cells that produce IFN-γ in response to recall antigens are one of the primary drivers of the DTH response (Black C A. 1999. *Delayed type hypersensitivity: current theories with an historic perspective*. Dermatol Online J 5:7). However, instead of injecting antigens into the skin, we monitored the production of IFN-γ using a technique called ELISpot to specifically detect IFN-γ producing T-cells following antigen presentation in vitro. Following incubation of splenocytes with specific antigens or controls, IFN-γ is captured by an antibody on the membrane and then detected using an enzyme-linked immuno-assay (the blue spots represent positives). As shown in FIG. 5, this assay measures robust responses of splenocytes from *T. gondii* infected mice incubated with ESA, while there is minimal response in naive animals. ConA is used as a non-specific stimulus as it evokes responses from all T-cells regardless of specific antigen presentation. We have adapted this assay for monitoring recombinant ESA proteins and peptides that are synthetically produced.

Example 8

Figure 6A:
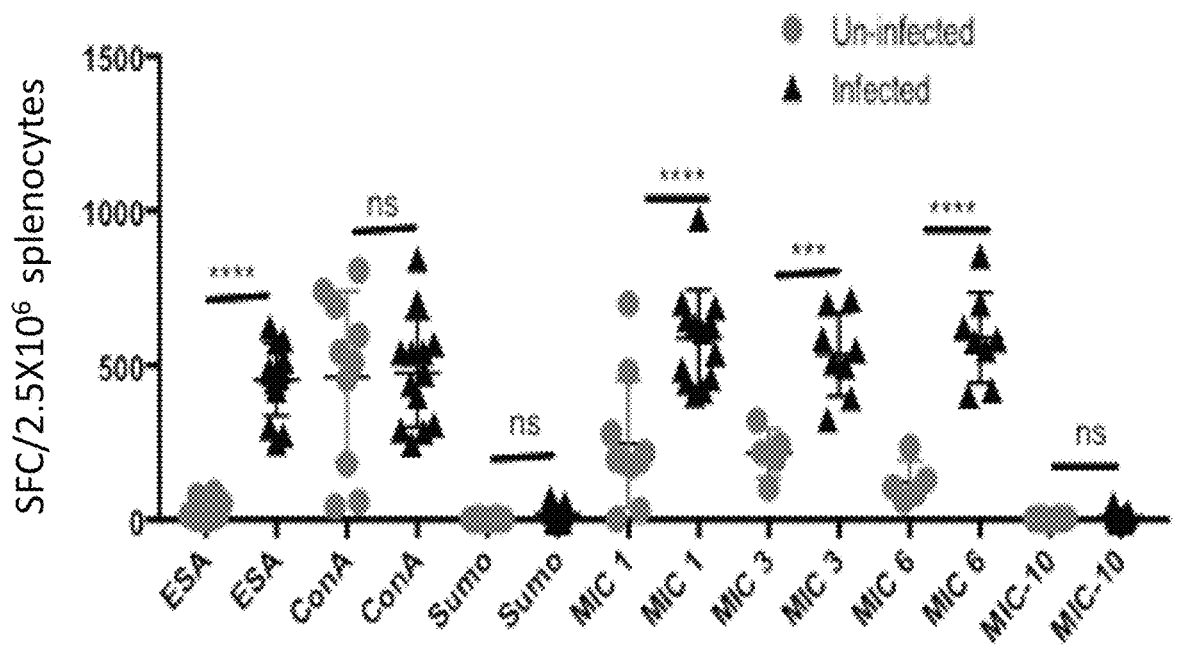
FIG. 6A-B shows ELISpot data for IFN-γ secretion by T cell in response to purified ESA proteins.
Figure 6B:
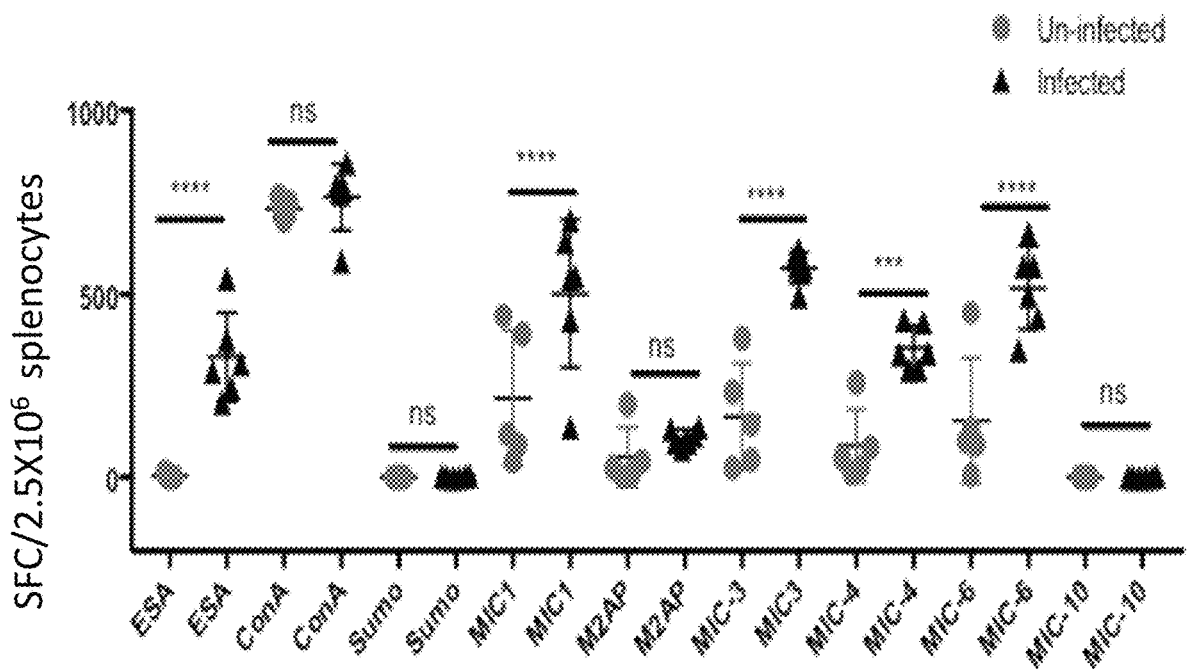

Using the ELISpot Assay to Monitor IFN-γ Secretion to Individual ESA Proteins The ELISpot assay was also used to examine the response of uninfected and chronically infected mice to individual ESA proteins that were produced recombinantly. Initially, the ESA fraction was compared to ConA as a positive control and SUMO as a negative control. High numbers of spot forming cells (SFC) were detected using an IFN-γ specific ELISpot assay as shown in FIG. 6. Individual ESA proteins were used at 3 micrograms per well in combination with $10^5$ splenocytes. Specific responses were detected to MIC1, MIC3, MIC4 and MIC6, but not to M2AP or to MIC10 as shown in FIG. 6. Similar responses were seen in infected C57/BL6 mice (FIG. 6A) and Balb/C mice (FIG. 6B).

References

The disclosure of each reference cited below and throughout this application is expressly incorporated herein.

References for Example 1

1. Brown, K. M., S. Lourido, and L. D. Sibley, *Serum Albumin Stimulates Protein Kinase G-dependent Microneme Secretion in Toxoplasma gondii*. J Biol Chem, 2016. 291(18): p. 9554-65.
2. Etheridge, R. D., et al., *ROP 18 and ROP 17 kinase complexes synergize to control acute virulence of Toxoplasma in the mouse*. Cell Host Microbe, 2014. 15: p. 537-550.
3. Behnke, M., et al., *Coordinated progression through two subtranscriptions underlies the tachyzoite cycle of Toxoplasma gondii*. Plos One, 2010. 5: p. e12354.
4. Khan, A., et al., *Geographic separation of domestic and wild strains of Toxoplasma gondii in French Guiana correlates with a monomorphic version of chromosome 1a*. Plos Negl. Trop. Dis., 2014. 8: p. e3182.
5. Gross, S., et al., *Bioluminescence imaging of myeloperoxidase activity in vivo*. Nat Med, 2009. 15(4): p. 455-61.

References for Examples 2-4

1. Carruthers V B, Sibley L D. 1997. Sequential protein secretion from three distinct organelles of *Toxoplasma gondii* accompanies invasion of human fibroblasts. Eur J Cell Biol 73:114-123.

2. Carruthers V B, Giddings O K, Sibley L D. 1999. Secretion of micronemal proteins is associated with *Toxoplasma* invasion of host cells. Cell Microbiol 1:225-236.
3. Carruthers V B, Moreno S N J, Sibley L D. 1999. Ethanol and acetaldehyde elevate intracellular [Ca2+] calcium and stimulate microneme discharge in *Toxoplasma gondii*. Biochem J 342:379-386.
4. Carruthers V B, Sibley L D. 1999. Mobilization of intracellular calcium stimulates microneme discharge in *Toxoplasma gondii*. Mol Microbiol 31:421-428.
5. Huynh M H, Barenau K E, Harper J M, Beatty W L, Sibley L D, Carruthers V B. 2003 Rapid invasion of host cells by *Toxoplasma* requires secretion of the MIC2-M2AP adhesive protein complex. EMBO J 22:2082-2090.
6. Brydges S D, Sherman G D, Nockemann S, Loyens A, Daubener W, Dubremetz J, Carruthers V B. 2000. Molecular characterization of TgMIC5, a proteolytically processed antigen secreted from the micronemes of *Toxoplasma gondii*. Mol Biochem Parasitol 111:51-66.
7. Hoff E F, Cook S H, Sherman G D, Harper J M, Ferguson D J, Dubremetz J F, Carruthers V B. 2001. *Toxoplasma gondii*: molecular cloning and characterization of a novel 18-kDa secretory antigen, TgMIC10. Exp Parasitol 97:77-88.
8. Mercier C, Cesbron-Delauw M F. 2015. *Toxoplasma* secretory granules: one population or more? Trends Parasitol 31:60-71.
9. Black C A. 1999. Delayed type hypersensitivity: current theories with an historic perspective. Dermatol Online J 5:7.
10. Allen I C. 2013. Delayed-type hypersensitivity models in mice. Methods Mol Biol 1031:101-107.
11. Rougier D, Ambroise-Thomas P. 1985. Detection of toxoplasmic immunity by multipuncture skin test with excretory-secretory antigen. Lancet 2:121-123.
12. Veprekova. 1978. Approximative molecular weight of the active component in toxoplasmin. Folia Parasitol (Praha) 25:273-275.
13. Frenkel J K. 1948. Dermal hypersensitivity to toxoplasma antigens (toxoplasmins). Proc Soc Exp Biol Med 68:634-639.
14. Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461

References for Examples 5-6

1 Carruthers V B, Sibley L D. 1997. Sequential protein secretion from three distinct organelles of *Toxoplasma gondii* accompanies invasion of human fibroblasts. Eur J Cell Biol 73:114-123.
2. Carruthers V B, Giddings O K, Sibley L D. 1999. Secretion of micronemal proteins is associated with *Toxoplasma* invasion of host cells. Cell Microbiol 1:225-236.
3. Carruthers V B, Moreno S N J, Sibley L D. 1999. Ethanol and acetaldehyde elevate intracellular [Ca2+] calcium and stimulate microneme discharge in *Toxoplasma gondii*. Biochem J 342:379-386.
4. Carruthers V B, Sibley L D. 1999. Mobilization of intracellular calcium stimulates microneme discharge in *Toxoplasma gondii*. Mol Microbiol 31:421-428.
5. Huynh M H, Barenau K E, Harper J M, Beatty W L, Sibley L D, Carruthers V B. 2003. Rapid invasion of host cells by *Toxoplasma* requires secretion of the MIC2-M2AP adhesive protein complex. EMBO J 22:2082-2090.
6. Brydges S D, Sherman G D, Nockemann S, Loyens A, Daubener W, Dubremetz J, Carruthers V B. 2000. Molecular characterization of TgMIC5, a proteolytically processed antigen secreted from the micronemes of *Toxoplasma gondii*. Mol Biochem Parasitol 111:51-66.
7 Hoff E F, Cook S H, Sherman G D, Harper J M, Ferguson D J, Dubremetz J F, Carruthers V B. 2001. *Toxoplasma gondii*: molecular cloning and characterization of a novel 18-kDa secretory antigen, TgMIC10. Exp Parasitol 97:77-88.
8. Mercier C, Cesbron-Delauw M F. 2015. *Toxoplasma* secretory granules: one population or more? Trends Parasitol 31:60-71.
9. Black C A. 1999. Delayed type hypersensitivity: current theories with an historic perspective. Dermatol Online J 5:7.
10. Allen I C. 2013. Delayed-type hypersensitivity models in mice. Methods Mol Biol 1031:101-107.
11. Rougier D, Ambroise-Thomas P. 1985. Detection of toxoplasmic immunity by multipuncture skin test with excretory-secretory antigen. Lancet 2:121-123.
12. Veprekova. 1978. Approximative molecular weight of the active component in toxoplasmin. Folia Parasitol (Praha) 25:273-275.
13. Frenkel J K. 1948. Dermal hypersensitivity to toxoplasma antigens (toxoplasmas]. Proc Soc Exp Biol Med 68:634-639.
14. Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461.

References for Example 7

1 Huynh M H, Barenau K E, Harper J M, Beatty W L, Sibley L D, Carruthers V B. 2003. Rapid invasion of host cells by *Toxoplasma* requires secretion of the MIC2-M2AP adhesive protein complex. EMBO J 22:2082-2090.
2. Brydges S D, Sherman G D, Nockemann S, Loyens A, Daubener W, Dubremetz J, Carruthers V B. 2000. Molecular characterization of TgMIC5, a proteolytically processed antigen secreted from the micronemes of *Toxoplasma gondii*. Mol Biochem Parasitol 111:51-66.
3. Hoff E F, Cook S H, Sherman G D, Harper J M, Ferguson D J, Dubremetz J F, Carruthers V B. 2001. *Toxoplasma gondii*: molecular cloning and characterization of a novel 18-kDa secretory antigen, TgMIC10. Exp Parasitol 97:77-88.
4. Mercier C, Cesbron-Delauw M F. 2015. *Toxoplasma* secretory granules: one population or more? Trends Parasitol 31:60-71.
5. Black C A. 1999. Delayed type hypersensitivity: current theories with an historic perspective. Dermatol Online J 5:7.
6. Allen I C. 2013. Delayed-type hypersensitivity models in mice. Methods Mol Biol 1031:101-107.
7 Rougier D, Ambroise-Thomas P. 1985. Detection of toxoplasmic immunity by multipuncture skin test with excretory-secretory antigen. Lancet 2:121-123.
8. Veprekova. 1978. Approximative molecular weight of the active component in toxoplasmin. Folia Parasitol (Praha) 25:273-275.
9. Frenkel J K. 1948. Dermal hypersensitivity to *toxoplasma* antigens (toxoplasmins). Proc Soc Exp Biol Med 68:634-639.

10. Gross S, Gammon S T, Moss B L, Rauch D, Harding J, Heinecke J W, Ratner L, Piwnica-Worms D. 2009. Bioluminescence imaging of myeloperoxidase activity in vivo. Nat Med 15:455-461.
11. Philpott D J, Girardin S E. 2004. The role of Toll-like receptors and Nod proteins in bacterial infection. Molec Immunol 41:1099-1108.
12. Jacobs D M, Morrison D C. 1977. Inhibition of the mitogenic response to lipopolysaccharide (LPS) in mouse spleen cells by polymyxin B. J Immunol 118:2127.
13. Nielsen M, Lund O, Buus S, Lundegaard C. 2010. WIC class II epitope predictive algorithms. Immunology 130: 319-328.
14. Wang P, Sidney J, Dow C, Mothe B, Sette A, Peters B. 2008. A systematic assessment of MHC class II peptide binding predictions and evaluation of a consensus approach. PLoS Comput Biol 4:e1000048.
15. Erskine C L, Krco C), Hedin K E, Borson N D, Kalli K R, Behrens M D, Heman-Ackah S M, von Hofe E, Wettstein P J, Mohamadzadeh M, Knutson K L. 2011. MHC class II epitope nesting modulates dendritic cell function and improves generation of antigen-specific CD4 helper T cells. J Immunol 187:316-324.

The invention claimed is:

1. An in vitro method of monitoring a T cell response in a T cell from a subject, wherein the subject has not been immunized against *Toxoplasma gondii*, the method comprising: contacting the T cell of the subject with a composition comprising
   a truncated MIC4 comprising the amino acids 58-231 of the amino acid sequence as set forth in SEQ ID NO: 55, or a sequence at least 90% identical thereto; and
   detecting or quantifying release of a cytokine.

2. The method of claim 1 wherein the response is a delayed-type hypersensitivity response.

3. The method of claim 1 wherein the response is release of a cytokine.

4. The method of claim 1 wherein the response is release of interferon-γ.

5. The method of claim 1 wherein the T cells are in peripheral blood mononuclear cells.

6. The method of claim 1 wherein the T cells are in a blood sample.

7. The method of claim 1 further comprising the step of detecting or quantifying release of interferon-γ.

* * * * *